(12) United States Patent
Mesallum

(10) Patent No.: US 9,295,771 B2
(45) Date of Patent: *Mar. 29, 2016

(54) ARTERIAL-VENOUS SWITCHING

(75) Inventor: Sameh Mesallum, Quincy, MA (US)

(73) Assignee: BRAVO BIOMED, INC., Rockland, MA (US)

( * ) Notice: Subject to any disclaimer, the term of this patent is extended or adjusted under 35 U.S.C. 154(b) by 698 days.

This patent is subject to a terminal disclaimer.

(21) Appl. No.: 13/550,651

(22) Filed: Jul. 17, 2012

(65) Prior Publication Data

US 2013/0184632 A1    Jul. 18, 2013

Related U.S. Application Data

(62) Division of application No. 12/015,038, filed on Jan. 16, 2008, now Pat. No. 8,221,342.

(60) Provisional application No. 60/880,604, filed on Jan. 16, 2007.

(51) Int. Cl.
  *A61M 5/00* (2006.01)
  *A61M 1/36* (2006.01)

(52) U.S. Cl.
  CPC .............. *A61M 1/36* (2013.01); *A61M 1/367* (2013.01); *A61M 1/3613* (2014.02)

(58) Field of Classification Search
  CPC ... A61M 1/36; A61M 1/3601; A61M 1/3603; A61M 1/3604; A61M 1/3606; A61M 1/3607; A61M 1/3609; A61M 1/361; A61M 1/3612; A61M 1/3613; A61M 1/3615; A61M 1/3616; A61M 1/3618; A61M 1/362; A61M 1/367
  USPC ............. 604/4.01–6.16, 8–10, 500, 507, 508, 604/509, 93.01, 96.01, 264
  See application file for complete search history.

(56) References Cited

U.S. PATENT DOCUMENTS

| | | | |
|---|---|---|---|
| 4,946,458 | A | 8/1990 | Harms et al. |
| 5,011,468 | A | 4/1991 | Lundquist et al. |
| 5,833,650 | A | 11/1998 | Imran |
| 5,908,407 | A | 6/1999 | Frazee et al. |
| 6,177,049 | B1 | 1/2001 | Schnell et al. |

(Continued)

FOREIGN PATENT DOCUMENTS

WO    2005061043 A1    7/2005

OTHER PUBLICATIONS

The Department of Urology, University Hospital Nijmegen, "Variability of Pressure-Flow Anaylsis Parameters in Repeated Cystometry in Patients with Benign Prostatic Hyperplasia," Peter F.W.M. Rosier, et al., Oct. 7, 1994.

(Continued)

*Primary Examiner* — Philip R Wiest
(74) *Attorney, Agent, or Firm* — Lando & Anastasi, LLP

(57) ABSTRACT

Methods and devices are provided for switching fluid flow through a body part, such as all or portions of an organ or extremity. In general, fluid inflow and fluid outflow vessels to at least a portion of a body part can be switched such that all fluid in at least a portion of the inflow and outflow vessels flows in an opposite direction. In other words, the fluid inflow vessel (or at least a portion thereof) becomes the fluid outflow vessel that receives fluid from a body part, and the fluid outflow vessel (or at least a portion thereof) becomes the fluid inflow vessel that delivers fluid to a body part.

30 Claims, 24 Drawing Sheets

(56) References Cited

U.S. PATENT DOCUMENTS

| | | |
|---|---|---|
| 6,386,202 B1 | 5/2002 | Frazee |
| 6,555,057 B1 | 4/2003 | Barbut et al. |
| 6,699,231 B1 * | 3/2004 | Sterman et al. ............... 604/509 |
| 6,887,227 B1 | 5/2005 | Barbut |
| 6,926,662 B1 | 8/2005 | Aboul-Hosn et al. |
| 2005/0131453 A1 | 6/2005 | Parodi |
| 2005/0228432 A1 | 10/2005 | Hogendijk et al. |

OTHER PUBLICATIONS

CoAxia, "NeuroFlo"TM, Front Line Treatment for Cerebral Ischemia (2 pp.), Printed from Website on Apr. 18, 2008.

W. L. Gore & Associates, May 2006, "The New Direction in Neuro Protection Flow Reversal," Flow Reversal Innovation by Juan Parodi (4 pp).

\* cited by examiner

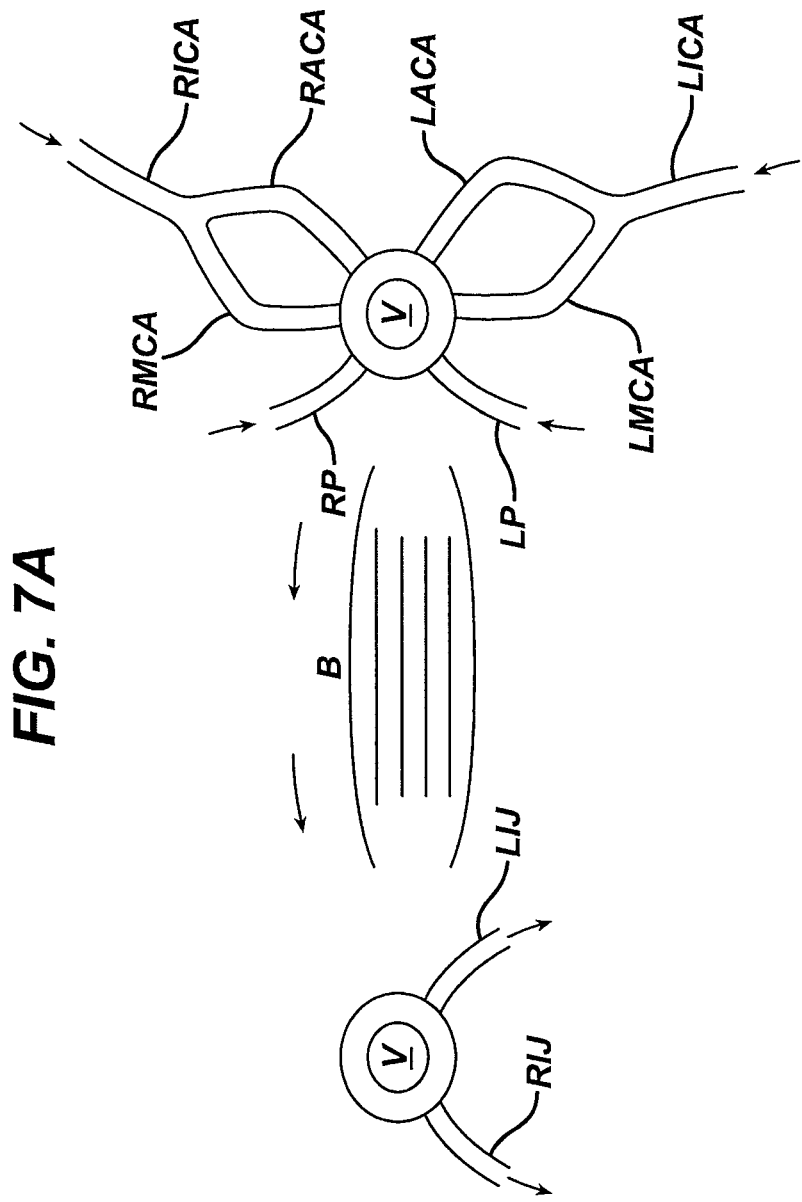

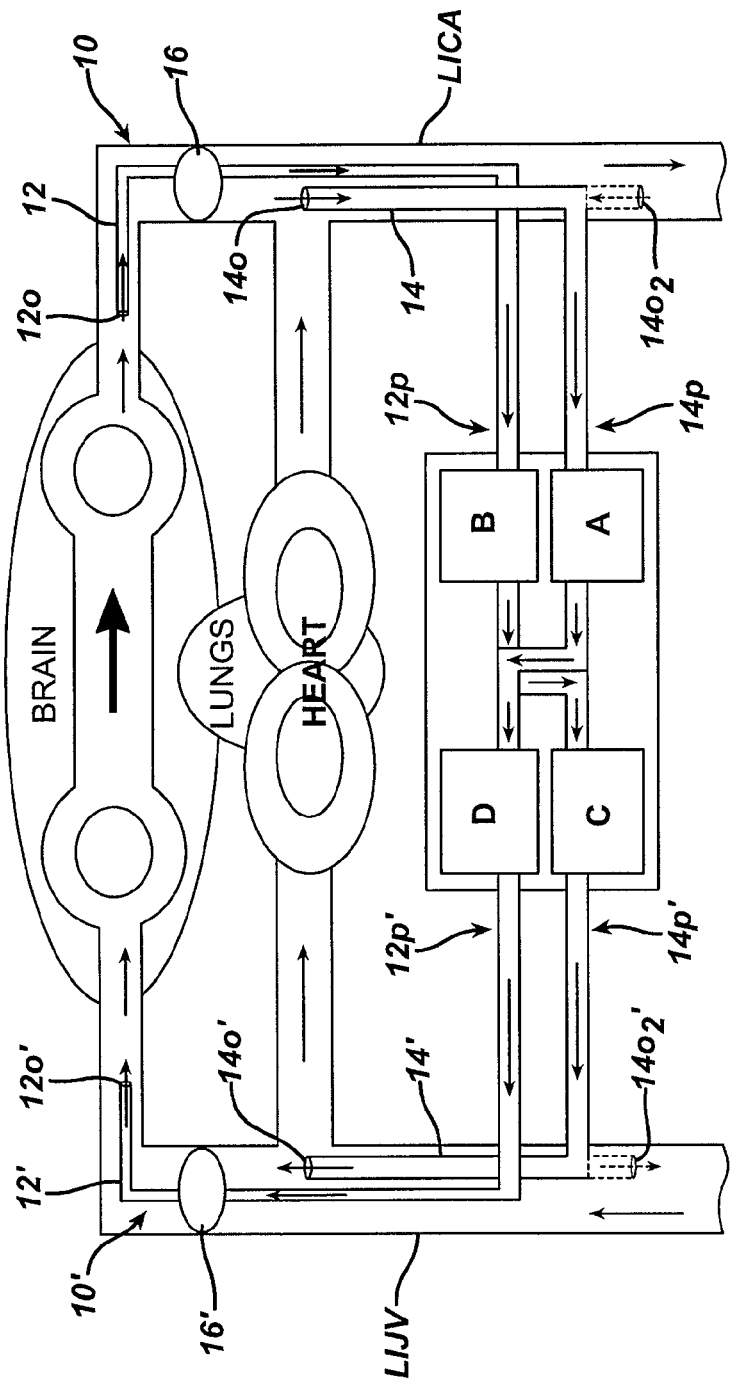

ARTERIAL-VENOUS SWITCHING

CROSS-REFERENCE TO RELATED APPLICATIONS

This application is a divisional application of and claims priority under 35 U.S.C. §120 to U.S. patent application Ser. No. 12/015,038, entitled "ARTERIAL-VENOUS SWITCHING," filed on Jan. 16, 2008, now U.S. Pat. No. 8,221,342 issued Jul. 17, 2012, which claims priority to U.S. Provisional Application No. 60/880,604 filed on Jan. 16, 2007 and entitled "Methods and Apparatus for Hydraulic Systems Control Inside the Body," which is hereby incorporated by reference in its entirety.

FIELD OF THE INVENTION

The present invention relates to methods and devices for switching fluid flow through a body part, such as an organ or extremity.

BACKGROUND OF THE INVENTION

Occlusion of arterial blood supply to various body parts can cause severe damage to vital structures, especially if the occlusion includes a large vessel, happened acutely or sub-acutely, and/or was prolonged. The main reason for organ or extremity damage is the lack of oxygen supply as well as other nutrients delivered by the arterial high pressure blood stream. With a stroke, for example, there is a rapidly developing loss of brain function due to a disturbance in the blood vessels supplying blood to the brain. Studies have shown that millions of brain cells die each minute following initial loss of blood flow to the brain.

Various techniques are known for reperfusing the occluded arterial supply, including direct mechanical reperfusion (balloon or dilator), elimination of occlusion (embolectomy or resection/anastomosis), bypassing the occlusion (CABG), reopening the occlusion (stent), pharmacologic dissolution (TP A for fibrinolysis, Heparin, Aspirin), etc. Each of these methods, has advantages and disadvantages. However, little progress has been observed where the occluded arterial supply is in a sensitive and surgically challenging location and the affected body part is irreversibly damaged in a short period, for example with a stroke. A thrombotic or embolic stroke can range from being totally asymptomatic to death. Large strokes tend to leave sever neurological deficits in the sensory and/or motor systems.

The pharmacologic treatment for a stroke, for example, is not as successful as in the case of the cardiac muscle. The use of fibrinolytic agents, namely TP A, should be achieved within a three hour window from incidence. There is also heightened risk of cerebral arterial or parenchymal bleeding that does not exist in the case of coronary reperfusion by TP A. The location and anatomy of the cerebral blood vessels make them more challenging to mechanical reperfusion by catheters, balloons, and/or stents. Surgical trials at embolectomy are tried in the case of large occlusion of a proximal cerebral blood vessel. Results are inconsistent due to the rapidity of brain cell injury and the irreversibility of their viable functions. The only networks of capillaries vasculature supplying the neuronal structures other than the arterial network include the venous and the lymphatic networks. Blood flows from the arterial side to small arteries named arterioles to end in a fine capillary network that supplies the tissues on cellular microscopic level. On the same level of capillaries, the venous network forms to collect venous blood and form bigger vessels named venules that eventually coalesce to form the cerebral veins. The lymphatic capillary network runs parallel to the venous system in general plus extra fluid system represented by the CSF circulation through specialized tissues surrounding the brain.

Accordingly, there remains a need for methods and devices for temporarily or permanently restoring oxygenated blood supply to affected body parts.

SUMMARY OF THE INVENTION

Methods and devices are provided for switching fluid flow through a body part, such as all or portions of an organ or extremity. In one embodiment, a method for switching fluid flow in a body part is provided and includes coupling a flow control system to a fluid inflow vessel and a fluid outflow vessel of a body part such that the flow control system causes all fluid from the fluid inflow and outflow vessels to flow into the body part through the fluid outflow vessel and to flow out of the body part through the fluid inflow vessel. The body part can be, for example, an organ and an extremity, and the fluid can be, for example, oxygenated blood. In certain exemplary embodiment, the fluid inflow and outflow vessels can be arterial and venous vessels.

In one embodiment, the flow control system can form blockages in the fluid inflow and outflow vessels and can redirect all fluid on proximal and distal sides of the blockages. The blockages in the fluid inflow and outflow vessels can each include a distal side in fluid communication with the body part and a proximal side blocked from fluid communication with the body part. The flow control system can redirect fluid from the proximal side of the fluid inflow vessel to the distal side of the fluid outflow vessel, and from the distal side of the fluid inflow vessel to the proximal side of the fluid outflow vessel. In one exemplary embodiment, the flow control system can include a housing for directing fluid into the body part through the fluid outflow vessel and out of the body part through the fluid inflow vessel. The flow control system can also include a pump coupled to the housing and configured to pump fluid through the housing.

In another embodiment, the body part can include first and second fluid inflow vessels and first and second fluid outflow vessels. Fluid can flow into the body part through the second fluid inflow vessel and fluid can flow out of the body part through the second fluid outflow vessel. The flow control system can be coupled to the first fluid inflow and outflow vessels such that all fluid from the first fluid inflow and outflow vessels flows into the body part through the first fluid outflow vessel and flows out of the body part through the first fluid inflow vessel.

The method can also include repeating the step of coupling for at least one additional body part to cause all fluid from the fluid inflow and outflow vessels of the at least one additional body part to flow into the at least one additional body part through the fluid outflow vessel and to flow out of the least one additional body part through the fluid inflow vessel.

In yet another embodiment, coupling a flow control system can include implanting a first balloon catheter in the fluid inflow vessel and a second balloon catheter in the fluid outflow vessel such that the first and second balloon catheters form blockages in the fluid inflow and outflow vessels and redirect all fluid flow through the fluid inflow and fluid outflow vessels. The first and second balloon catheters can each include a proximal port positioned on a proximal side of a balloon forming the blockage, and a distal port positioned on a distal side of a balloon forming the blockage. The proximal ports can be blocked from fluid communication with the body part and the distal ports can be in fluid communication with the body part.

In another embodiment, the body part can be the brain and the flow control system can be coupled to the arterial and venous blood pathways coupled to the brain. Coupling the flow control system can include advancing a first catheter through the femoral artery and forming a blockage within the internal carotid artery, and advancing a second catheter through the femoral vein and forming a blockage within the internal jugular vein. Blood flowing from the heart and into the internal carotid artery on a proximal side of the blockage will thus flow through a first lumen in the first catheter and through a first lumen in the second catheter and be delivered to a distal side of the blockage in the internal jugular vein such that the blood flows into the brain from the internal jugular vein, and blood flowing from the brain and into the internal carotid artery on a distal side of the blockage will flow through a second lumen in the first catheter and through a second lumen in the second catheter and be delivered to a proximal side of the blockage in the internal jugular vein such that the blood flows from the internal jugular vein toward the heart. The first and second catheters can optionally be coupled to a pump that pumps blood through the catheters. In one embodiment, the pump can apply a negative pressure to the distal side of the first catheter such that a pressure of the arterial pathway to the brain is neutralized to cause all blood flow into the brain from the arterial pathway to flow out of the brain and into the brain through the venous pathway.

In another embodiment, the body part can be the heart and the flow control system can be coupled to the heart such that blood flows from the left side of the heart to the right side of the heart. Alternatively, the body part can be the heart and the flow control system can be coupled to the heart such that blood exits the heart through the coronary artery and blood enters the heart through the coronary sinus. In another embodiment, the body part can be the lower extremity and the flow control system can be coupled to the lower extremity such that blood exits the lower extremity through the femoral artery and blood enters the lower extremity through the femoral vein. Similarly, the body part can be the upper extremity and the flow control system can be coupled to the upper extremity such that blood exits the upper extremity through the brachial artery and blood enters the upper extremity through the brachial vein. Alternatively, the body part can be the upper extremity and the flow control system can be coupled to the upper extremity such that blood exits the upper extremity through the subclavian arteries and blood enters the upper extremity through the subclavian veins. In another embodiment, the fluid inflow vessel can be an arterial vessel and fluid outflow vessel can be a lymphatic vessel, and the flow control system can be coupled such that blood enters the body part through the lymphatic vessel and blood exits the body part through a venous vessel. Alternatively, the fluid inflow vessel can be an arterial vessel and fluid outflow vessel can be a lymphatic vessel, and the flow control system can be coupled such that blood enters the body part through the lymphatic vessel and a venous vessel and blood exits the body part through the arterial vessel. In yet another embodiment, the body part can be the liver and the flow control system can be coupled to the liver such that blood enters the liver through the hepatic veins and blood exits the liver through the hepatic artery and portal vein. In other aspects, the body part can be the lungs and the flow control system can be coupled to the lungs such that blood enters the lungs through the pulmonary veins and blood exits the lungs through the pulmonary arteries.

In another embodiment, a method for switching blood flow in a body part is provided and includes delivering oxygenated blood flowing into a body part to a blood outflow vessel of the body part and delivering oxygenated blood flowing out of the body part into a blood inflow vessel of the body part such that all oxygenated blood enters the body part through the blood outflow vessel and all oxygenated blood exits the body part through the blood inflow vessel. In one embodiment, oxygenated blood is delivered using at least two catheters that are implanted to form blockages in the blood inflow and outflow vessels. A negative pressure can be generated in at least one of the catheters to cause all oxygenated blood to enter the body part through the blood outflow vessel and all oxygenated blood to exit the body part through the blood inflow vessel. In another embodiment, each blockage can include a distal side in fluid communication with the body part and a proximal side blocked from fluid communication with the body part, and the at least two catheters can redirect fluid from the proximal side of the blood inflow vessel to the distal side of the blood outflow vessel, and from the distal side of the blood inflow vessel to the proximal side of the blood outflow vessel. In certain exemplary embodiments, oxygenated blood is delivered using a pump mechanism.

In another aspect, a method for switching blood flow in an arterial-venous system is provided and includes forming a first blockage in a blood inflow vessel that delivers blood to a body part to prevent blood flow between a distal side of the first blockage in fluid communication with the body part and a proximal side of the first blockage blocked from communication with the body part, forming a second blockage in a blood outflow vessel that drains blood from the body part to prevent blood flow between a distal side of the second blockage in fluid communication with the body part and a proximal side of the second blockage blocked from communication with the body part, and redirecting blood from the proximal side of the first blockage into the distal side of the second blockage, and from the distal side of the first blockage into the proximal side of the second blockage such that blood flow through the body part is switched.

In one embodiment, forming the first blockage can include positioning a first catheter within the blood inflow vessel and inflating a balloon on the first catheter to form the first blockage, and forming the second blockage can include positioning a second catheter within the blood outflow vessel and inflating a balloon on the second catheter to form the second blockage. The first and second catheters can each include at least one lumen formed therein that redirects blood. In an exemplary embodiment, blood flows from the body part into a first lumen of the first catheter and out of a second lumen of the second catheter and into the blood outflow vessel, and from the blood inflow vessel into a second lumen of the first catheter and out of a first lumen of the second catheter and into the body part. The method can also include forming a third blockage in a second blood inflow vessel that delivers blood to a body part to prevent blood flow between a distal side of the third blockage in fluid communication with the body part and a proximal side of the third blockage blocked from communication with the body part, and forming a fourth blockage in a second blood outflow vessel that drains blood from the body part to prevent blood flow between a distal side of the fourth blockage in fluid communication with the body part and a proximal side of the fourth blockage blocked from communication with the body part. The method can also optionally include activating a pumping mechanism to redirect blood flow.

In certain exemplary embodiment, the blood inflow and outflow vessels comprise arterial and venous vessels. In one embodiment, the body part can be the brain and the blood inflow vessel can be the carotid artery and the blood outflow vessel comprises the jugular vein. The first blockage can be formed by advancing a first catheter through the femoral artery to position a balloon on the first catheter within the carotid artery, and inflating the balloon to form the first blockage within the carotid artery, and the second blockage can be formed by advancing a second catheter through the femoral vein to position a balloon on the second catheter within the jugular vein, and inflating the balloon to form the second blockage within the carotid artery. Blood flowing from the heart and into the carotid artery on a proximal side of the first blockage can flow through a first lumen in the first catheter and through a first lumen in the second catheter and is delivered to a distal side of the second blockage in the jugular vein such that the blood flows into the brain from the jugular vein, and blood flowing from the brain and into the carotid artery on a distal side of the first blockage can flow through a second lumen in the first catheter and through a second lumen in the second catheter and is delivered to a proximal side of the second blockage in the jugular vein such that the blood flows from the jugular vein toward the heart.

In other embodiments, the body part can be the heart and the first and second blockages are formed such that blood flows from the left side of the heart to the right side of the heart, or such that blood exits the heart through the coronary artery and enters the heart through the coronary sinus. In another embodiment, the blood inflow vessel can be an arterial vessel and the blood outflow vessel can be a lymphatic vessel, and the first and second blockages can be formed such that blood enters the body part through the lymphatic vessel and blood exits the body part through a venous vessel, or such that blood enters the body part through the lymphatic vessel and a venous vessel and blood exits the body part through the arterial vessel. In another embodiment, body part can be the liver and the first and second blockages are formed such that blood enters the liver through the hepatic veins and blood exits the liver through the hepatic artery and portal vein, or it can be the lungs and the first and second blockages are formed such that blood enters the lungs through the pulmonary veins and blood exits the lungs through the pulmonary arteries.

A method for switching blood flow is also provided according to another embodiment, and includes forming a blockage in an artery, wherein blood normally flows toward the blockage on a first side of the blockage and blood normally flows away from the blockage on a second side of the blockage, and forming a blockage in a vein, wherein blood flows toward the blockage on a first side of the blockage and blood flows away from the blockage on a second side of the blockage. Blood can be delivered from the first side of the blockage in the artery to the first side of the blockage in the vein and from the second side of the blockage in the artery to the second side of the blockage in the vein such that blood flow on the second side of the artery and the first side of the vein is switched to flow toward the blockage on the second side of the artery and to flow away from the blockage on the first side of the vein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 7A is a diagram illustrating normal blood flow through the brain from left and right arterial supplies to left and right venous supplies;

FIG. 7D is a diagram illustrating blood flow through the brain switched by the flow control system such that blood flows into the brain from the venous supply and blood exits the brain through the arterial supply;

DETAILED DESCRIPTION OF THE INVENTION

Figure 1:
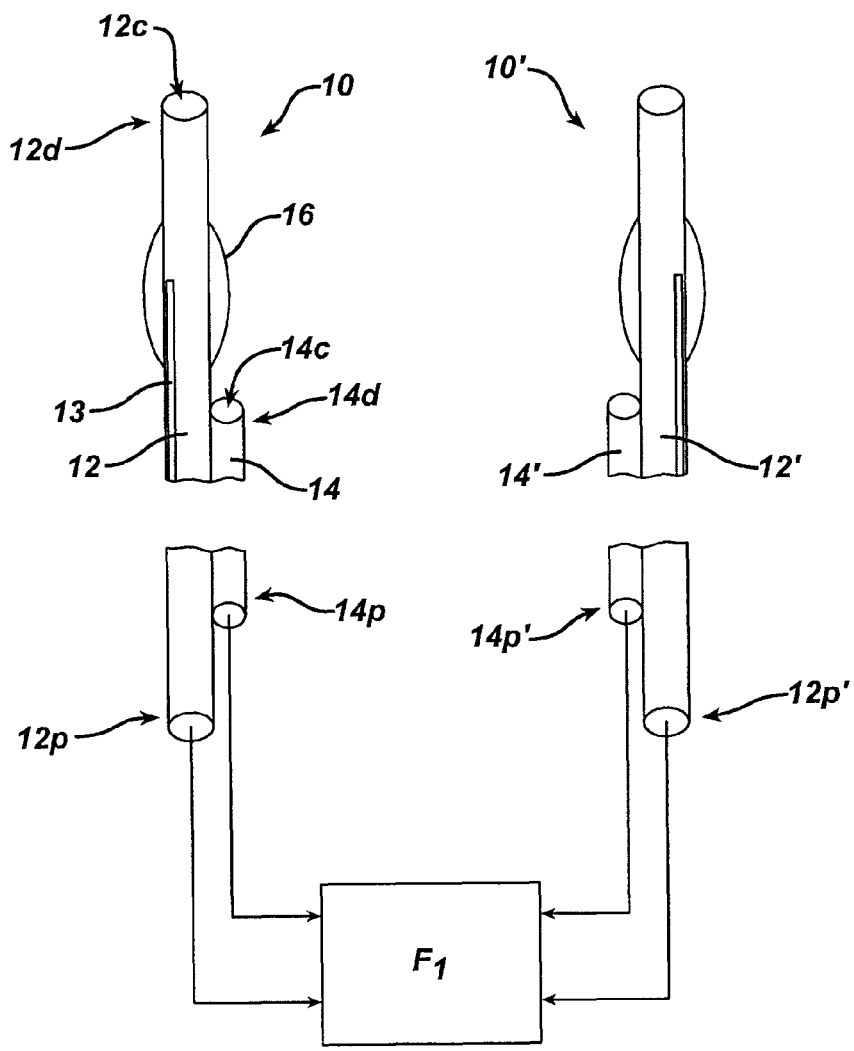
FIG. 1 is a partially transparent perspective view of one embodiment of a flow control system having first and second catheters coupled to a flow control apparatus.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

The present invention generally provides methods and devices for switching fluid flow through a body part, such as all or portions of an organ or extremity. In general, fluid inflow and fluid outflow vessels to at least a portion of a body part can be switched such that all fluid in at least a portion of the inflow and outflow vessels flows in an opposite direction. In other words, the fluid inflow vessel (or at least a portion thereof) becomes a fluid outflow vessel that receives fluid from a body part, and the fluid outflow vessel (or at least a portion thereof) becomes a fluid inflow vessel that delivers fluid to a body part. By switching the direction of fluid flow through at least a portion of a body part, various beneficial results can be achieved. For example, in certain exemplary embodiments, the fluid can be blood, and more preferably oxygenated blood, and the inflow and outflow vessels can be arterial and venous vessels. Switching blood flow through at least a portion of arterial and venous vessels can be accomplished by allowing the healthy venous vessels to act as arterial vessels (or vice versa), thus overcoming problems due to blockage or deterioration. Occlusion of the arterial blood supply to a body part can cause severe damage to vital structures, especially where the occlusion is located in a large vessel, happened acutely or subacutely, and was prolonged. The main reason damage to the organ occurs is because of the lack of oxygen as well as other nutrients delivered by the arterial high pressure blood stream. Thus, switching the blood flow allows the blood to reach the organ through the venous pathway, thereby avoiding any further damage to the organ. With the brain, for example, switching oxygenated blood flow into and out of the brain, or at least portions thereof, can prevent further damage from a stroke, since oxygenated blood is now capable of reaching the brain through the fluid outflow vessels (e.g., the venous vessels). Similar benefits can be achieved in various other organs, such as the heart, lungs, liver, etc., as well as in various extremities, such as portions or all of the upper and lower extremities.

While various techniques can be used to switch fluid flow to a body part, in an exemplary embodiment a flow control system is provided and it is configured to form at least one blockage in at least one vessel and to redirect fluid flow through the vessel(s). While the flow control system can have virtually any configuration, in one embodiment the system includes one or more balloon catheters. A person skilled in the art will appreciate that various other hollow elongate members having various expandable elements formed thereon can be used in place of the balloon catheters discussed herein. FIG. 1 illustrates one exemplary embodiment of a balloon catheter, showing two balloon catheters 10, 10' coupled to a flow control apparatus F1. Only one of the balloon catheters 10 will be discussed in detail, as the other catheter 10' can have the same or similar configuration. A person skilled in the art will appreciate that, while two identical balloon catheters are shown, different devices can be used in conjunction with one another.

As shown in FIG. 1, the balloon catheter 10 includes a first tubular member 12 with a lumen 12c extending therethrough and a second tubular member 14 coupled to the first tubular member 12 and having a lumen 14c extending therethrough. One of the tubular members, e.g., the first tubular member 12, can also include an inflation lumen 13, which in the illustrated embodiment is formed in a sidewall thereof, for allowing an inflation fluid, such as air or liquid, to be delivered to an expandable balloon 16 disposed there around for forming a blockage in a pathway. As further shown in FIG. 1, in an exemplary embodiment a distal end 14d of the second tubular member 14 is positioned proximal to the expandable balloon 16 on the first tubular member 12, and the expandable balloon 16 is positioned proximal to a distal end 12d of the first tubular member 12. Such a configuration allows an opening formed in the distal end 12d of the first tubular member 12 to be positioned on one side of the expandable balloon 16 while an opening formed in the distal end 14d of the second tubular member 14 is positioned on an opposite side of the expandable balloon 16. In use, the openings are thus positioned on opposed sides of a blockage formed in a pathway by the expandable balloon 16. A proximal end 12p, 14p of each tubular member 12, 14 can be coupled to the flow control apparatus F1, as will be discussed below. A person skilled in the art will appreciate that the particular configuration of the catheter and the lumens extending therethrough can vary. For example, while the illustrated catheter is shown having two tubular members coupled to one another, in other embodiments a single tubular member can be used with multiple lumens extending therethrough. Accordingly, the term tubular member is intended to include both separate and distinct tubular members that are coupled to one another, and separate and distinct lumens formed through a single tubular member, i.e., a multi-lumen catheter.

The flow control apparatus F1, which is generically represented by a box, can be configured to direct fluid flow between the proximal ends of any number of balloon catheters used with the system. In the illustrated embodiment, the flow control apparatus F1 can direct fluid from the proximal ends 12$p$, 14$p$ of the first and second tubular members 12, 14 of the first balloon catheter 10 to the proximal ends 12$p'$, 14$p'$ of the first and second tubular members 12', 14' of the second balloon catheter 10'. The flow control apparatus F1 can have virtually any configuration for directing fluid flow. For example, it can be a housing with pathways extending therethrough for directing fluid flow from, for example, the proximal end 12$p$ of the first tubular member 12 on the first balloon catheter 10 to the proximal end 14$p'$ of the second tubular member 14' on the second balloon catheter 10', etc. In other embodiments, the flow control apparatus F1 can include a control mechanism for allowing a user to selectively control the couplings between the proximal ends of the tubular members on each catheter coupled to the apparatus. Such a configuration could include, for example, one or more dials and/or valves that direct fluid flow through the apparatus thus allowing user control over the direction of fluid flow. The fluid control system can also include other features, such as a pump mechanism disposed within or coupled to the flow control apparatus F1 for controlling a rate of fluid flow through the apparatus, a recirculating pathway and/or pump for recirculating fluid through the apparatus, and/or one or more drug delivery mechanisms for allowing various drugs to be injected into the fluid and delivered to a desired location. The flow control system could also include features that would allow various other therapies to be delivered and/or performed, such as dialysis, etc. The flow control system can also optionally control various parameters in addition to flow rate, pressure, and/or chemical or pharmacological composition, such as pulsation, resonance, temperature, and addition or subtraction of components such as blood cells, electrolytes, etc. A person skilled in the art will appreciate that the flow control apparatus 10 can have virtually any configuration, and the particular configuration can vary based on the intended use. Moreover, the flow control apparatus 10 need not be a separate housing that is coupled to the balloon catheters 10, 10', but rather the proximal ends 12$p$, 14$p$, 12$p'$, 14$p'$ of the balloon catheters 10, 10' can be configured to directly couple to one another to allow a direction of fluid flow to be controlled. The fluid flowing through the system can also be separated or it can be mixed within the system. The system can also be configured to be fully implantable, or various components can remain external to the system. The particular configuration can vary based on the whether the system is intended for acute, semi-acute, or long-term/permanent use. While not shown, the system can include other features such as one or more pressure sensors for sensing the fluid pressure within the system and/or expandable balloon.

In use, the flow control system can allow fluid flow through at least a portion of a body part to be totally switched. A person skilled in the art will appreciate that the body part can include any body part that receives fluid flow therethrough, such as all or certain portions of an organ, vessel, and/or extremity. For example, the body part can be all or certain portions of the brain, heart, lungs, liver, kidney, limb such as an arm or leg, portions of vessels, eye, intestine, adrenal gland, or other regions of the body. The fluid can be any bodily fluid, but in certain exemplary embodiments the fluid is blood, and more preferably oxygenated blood. The term "inflow" vessel is intended to refer to those vessels that naturally deliver fluid to a body part and the term "outflow" vessel is intended to refer to those vessels that naturally receive fluid from a body part. Typically, all body parts have fluid flowing therethrough which is delivered to the body part by an artery and which exits the body part through a vein. Thus, in certain exemplary embodiments, fluid flow is switched by switching the arterial and venous supplies to a body part. The present invention allows the fluid flow through all or a portion of a body part to be switched such that the inflow vessel acts as an outflow vessel and the outflow vessel acts as an inflow vessel. FIGS. 2A-6E illustrate various exemplary configurations for switching fluid flow.

Figure 2A:
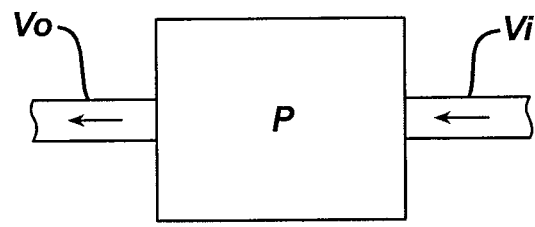
FIG. 2A is a diagram illustrating normal fluid flow through a body part from a fluid inflow vessel to a fluid outflow vessel.
Figure 2B:
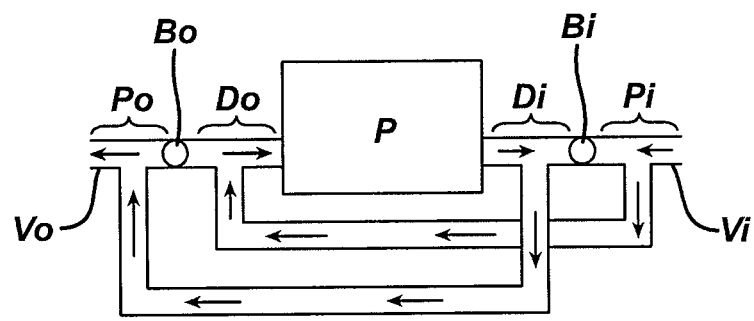
FIG. 2B is a diagram illustrating the fluid flow through the body part of FIG. 2A switched such that fluid flows into the body part from the outflow vessel and fluid exits the body part through the inflow vessel.

FIGS. 2A-2B illustrate one exemplary configuration for switching fluid flow through a fluid inflow supply and a fluid outflow supply. FIG. 2A illustrates normal fluid flow, showing a fluid inflow vessel Vi for delivering fluid to a body part P, generically represented as a box, and a fluid outflow vessel Vo for receiving fluid flow from the body part P. During normal fluid flow the fluid flows into the body part P from the inflow vessel Vi, and fluid flows away from the body part P through the outflow vessel Vo, as indicated by the arrows in FIG. 2A. With a typical body part, such as the brain, heart, or a limb, blood is delivered to the body part through an arterial vessel and blood flows away from the body part through a venous vessel. In order to switch fluid flow going into and out of the body part, the fluid can be redirected. In particular, as shown in FIG. 2B, a blockage Bi, Bo can be formed in each of the fluid inflow and fluid outflow vessels Vi, Vo to fully block fluid flow therethrough. As indicated above, an expandable balloon on a balloon catheter can be used to form each blockage Bi, Bo, however various other techniques for forming the blockages can also be used. During normal fluid flow in the inflow vessel Vi, fluid will flow toward the blockage Bi on the proximal side Pi of blockage Bi and away from the blockage Bi on the distal side Di of the blockage Bi. As used herein, the term proximal will refer to the side of the blockage that is blocked from communication with the body part P, and the term distal will refer to the side of the blockage that is in fluid communication with the body part P. The terms proximal and distal are not intended to refer to particular anatomical locations, and thus in some cases the terms proximal and distal will refer to a portion of a vessel in the body that is not necessarily anatomically located proximal or distal to the body part. During normal fluid flow in the outflow vessel Vo, fluid will flow away from the blockage Bo on the proximal side Po of blockage Bo (i.e., the side blocked from communication with the body part P) and toward the blockage Bo on the distal side Do of the blockage Bo (i.e., the side in fluid communication with the body part P). Once the blockages Bo, Bi are formed, the fluid flow can be switched, at least for a portion of the inflow and outflow vessels Vi, Vo, e.g., the portion located on the distal side of each blockage Bi, Bo, to allow fluid to flow into the body part P from the outflow vessel Vo and to flow out of the body part P through the inflow vessel Vi. This can be achieved without affecting the direction of fluid flow on the proximal side Pi, Po of each blockage Bi, Bo, thus allowing fluid flow through other parts of the body to remain unaffected. In order to achieve such switching, as shown in FIG. 2B fluid in the proximal side Pi of the blockage Bi in the inflow vessel Vi can be redirected and delivered to the distal side Do of the blockage Bo in the outflow vessel Vo, and fluid in the distal side Di of the inflow vessel Vi can be redirected and delivered to the proximal side Po of the blockage Bo in the outflow vessel Vo.

While FIG. 2B generally illustrates two pathways for redirecting and delivering the fluid, as indicated above the pathways can be in the form of one or more lumens formed in a balloon catheter. For example, the expandable balloon 16 on the first catheter 10 of FIG. 1 can be used to form the blockage Bi in the inflow vessel Vi such that the opening in the distal end 12d of the first tubular member 12 is positioned in fluid communication with the body part B (i.e., on the distal side Di of the blockage), and the opening in the distal end 14d of the second tubular member 14 is positioned on an opposite side of the blockage Bi (i.e., on the proximal side Pi of the blockage) and is thus blocked from fluid communication with the body part B. Fluid on the proximal side Pi of the blockage Bi in the inflow vessel will thus flow into the lumen 14c in the second tubular member 14 and fluid on the distal side Di of the blockage Bi in the inflow vessel will thus flow into the lumen 12c in the first tubular member 12. A second catheter can likewise be implanted in the fluid outflow vessel Vo. Thus, while FIG. 2B illustrates pathways extending directly from the distal side Di, Do of the inflow and outflow vessels Vi, Vo, a person skilled in the art will appreciate that the pathways are merely representative, and that, when a balloon catheter is implanted the lumens will form the pathways. Such a configuration is equally applicable to FIGS. 2C-5C.

As a result of the fluid being redirected, fluid flowing in its normal direction toward the blockage Bi on the proximal side Pi of the blockage Bi in the inflow vessel Vi will be delivered to the distal side Do of the blockage Bo in the outflow vessel Vo, and will thus flow into the body part P through the outflow vessel Vo, thus switching the direction of fluid flow in the distal side Do of the outflow vessel Vo. The fluid will pass through the body part P and will exit the body part P and flow into the inflow vessel Vi, thus switching the direction of fluid flow in the distal side Di of the inflow vessel Vi. The fluid flowing from the body part P into the distal side Di of the inflow vessel Vi will be delivered to the proximal side Po of the outflow vessel Vo, where it will flow away from the blockage Bo in its normal direction.

Figure 2C:
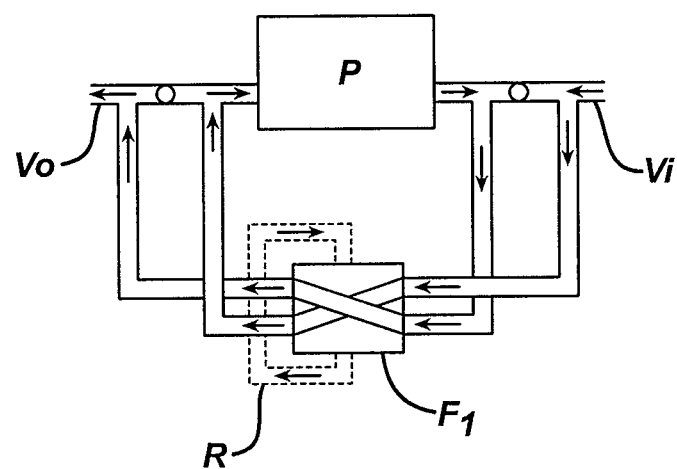
FIG. 2C is a diagram illustrating the configuration of FIG. 2B, showing a flow control apparatus coupled thereto for directing fluid flow.

FIG. 2C illustrates the switching configuration shown in FIG. 2B, except that a flow control apparatus F1 is shown coupled to the pathways for redirecting fluid. As shown, the flow control apparatus F1 directs fluid therethrough in a desired direction, coupling the pathways to achieve a desired result. The illustrated flow control apparatus F1 also includes a fluid recirculation pathway R that is configured to continuously recirculate fluid flowing through the flow control apparatus F1. This is particular desirable where the flood is blood, as any stagnant blood can clot causing further problems. The recirculation pathway can also include a filter for filtering the blood, or other features to facilitate use of the device.

Figure 3A:
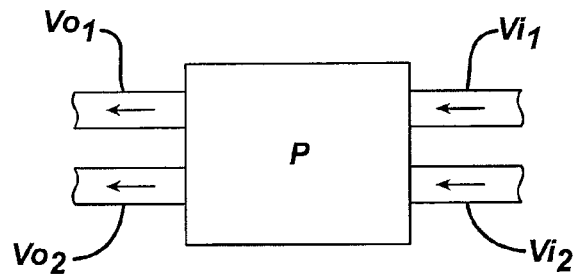
FIG. 3A is a diagram illustrating normal fluid flow through a body part from two fluid inflow vessels to two fluid outflow vessels.
Figure 3B:
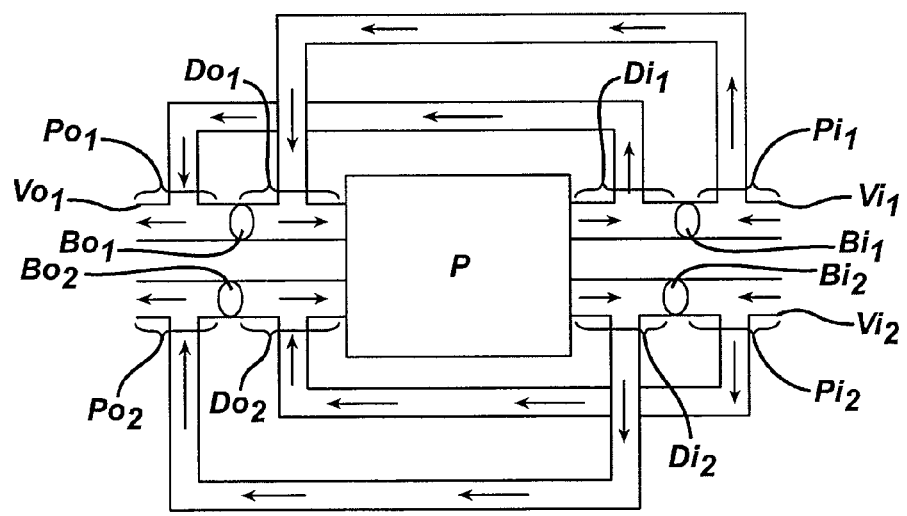
FIG. 3B is a diagram illustrating all fluid flow through the body part of FIG. 3A switched such that fluid flows into the body part from the outflow vessels and fluid exits the body part through the inflow vessels.
Figure 3C:
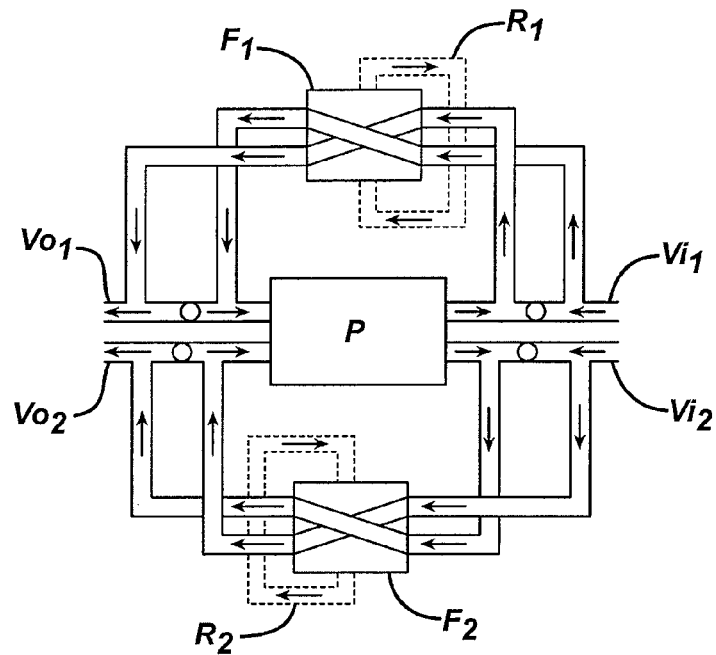
FIG. 3C is a diagram illustrating the configuration of FIG. 3B, showing first and second flow control apparatus coupled to the inflow and outflow vessels for directing fluid flow.
Figure 3D:
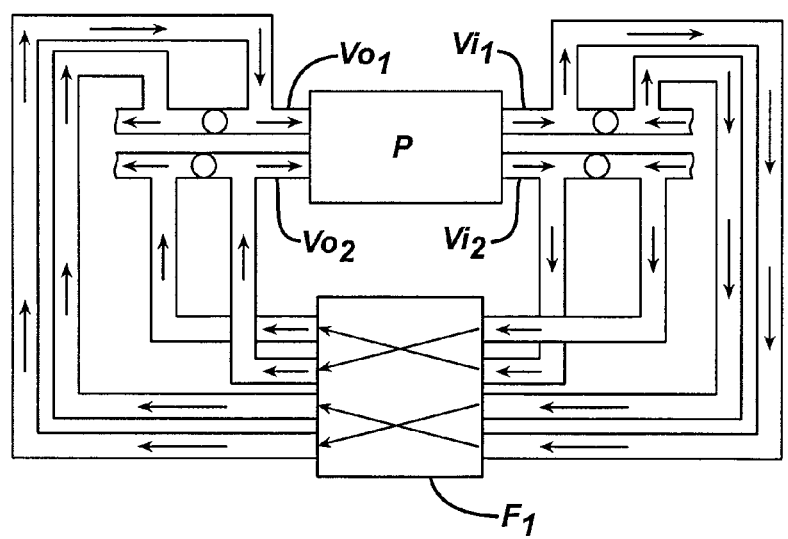
FIG. 3D is a diagram illustrating the configuration of FIG. 3B, showing only one flow control apparatus coupled to one inflow vessel and one outflow vessel for directing fluid flow.

Switching can be achieved in any number of vessels flowing into and out of a body part, and the particular configuration can depend on the particular body part. For example, in one embodiment fluid flow can be switch in an entire body part. In particular, the fluid in all of the inflow vessels normally flowing into a body part can be switched such that all inflow vessels receive fluid from the body part (i.e., they become outflow vessels), and likewise all fluid in all of the outflow vessels normally receiving fluid from the body part can be switched such that all outflow vessels deliver fluid to the body part (i.e., they become inflow vessels). This can be achieved by coupling a flow control system, as will be discussed in more detail below, to only one of multiple inflow and outflow vessels and configuring the system to switch fluid through all of the vessels, or by coupling the system to all of the inflow and outflow vessels. By way of non-limiting example, FIGS. 3A-3D illustrate one method for switching all fluid flow into a body part P having two inflow vessels ViI, Vi2 and two outflow vessels VO1, V02. As shown in FIG. 3A, during normal fluid flow all fluid is delivered into the body part P through the fluid inflow vessels ViI, Vi2, and all fluid exits the body part P through the fluid outflow vessels VO1, V02. As with the embodiment discussed above with respect to FIG. 2B, fluid flow can be switched by forming a blockage Bi1, Bi2, Bo1, B02 in each vessel ViI, Vi2, VO1, V02, and then redirecting the fluid flow to cause all fluid in the proximal side Pi1, Pi2 of the inflow vessels ViI, Vi2 to be delivered to the distal side Do1, D02 of the outflow vessels VO1, V02, and to cause all fluid in the distal side Di1, Di2 of the inflow vessels ViI, Vi2 to be delivered to the proximal side POI, P02 of the outflow vessels VO1, V02. As a result, fluid will flow into the body part P from the distal side DO1, D02 of the fluid outflow vessels VO1, V02, and fluid will flow out of the body part P and into the distal side Di1, Di2 of the fluid inflow vessels ViI, Vi2, and thus fluid flow is switched in the distal sides Di1, Di2, DO1, D02 of the inflow and outflow vessels ViI, Vi2, VO1, V02. Fluid flow will remain the same in the proximal sides Pi1, Pi2, POI, P02 of the inflow and outflow vessels ViI, Vi2, VO1, V02. FIG. 3C illustrates the switching configuration of FIG. 3B, showing a first flow control apparatus F1 coupled to the first inflow and outflow vessels ViI, VO1 and having a fluid recirculation pathway R1 coupled thereto, and a second flow control apparatus F2 coupled to the second inflow and outflow vessels Vi2, V02 and having a fluid recirculation pathway R2 coupled thereto, as similarly discussed above with respect to FIG. 2e. In another embodiment, a single flow control apparatus F1 can be coupled to all of the inflow and outflow vessels ViI, Vi2, VO1, V02, as shown in FIG. 3D.

Figure 4A:
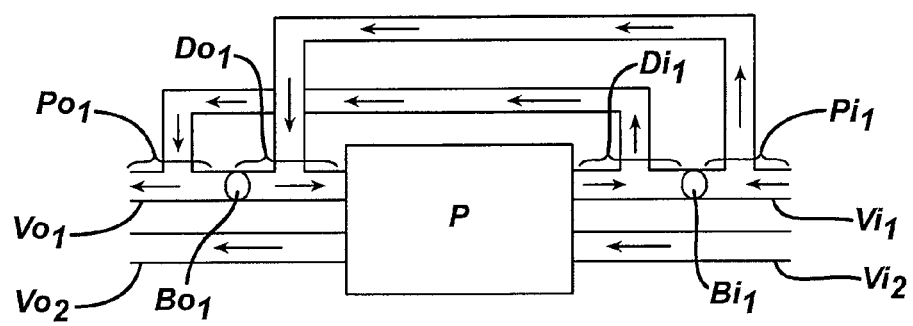
FIG. 4A is a diagram illustrating fluid flow through one of the inflow vessels and one of the outflow vessels of the body part of FIG. 3A switched such that fluid flows into the body part from one of the outflow vessels and fluid exits the body part through one of the inflow vessels while the other inflow and outflow vessels flow in a normal direction.
Figure 4B:
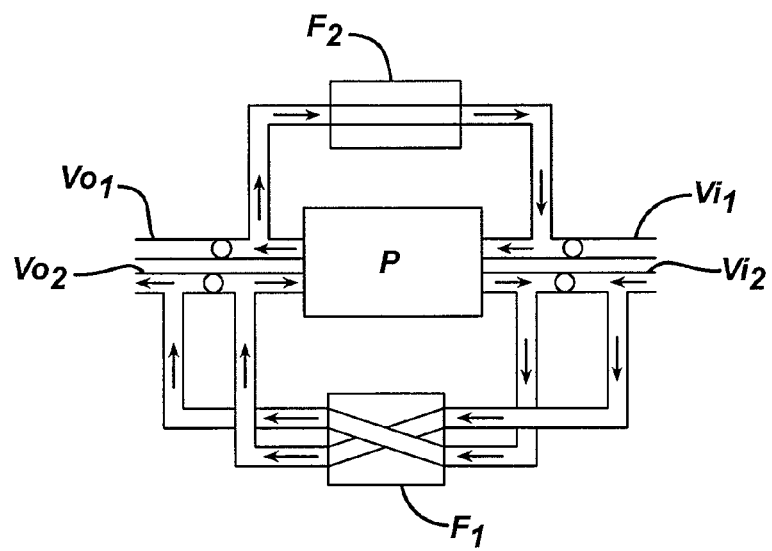
FIG. 4B is a diagram illustrating the configuration of FIG. 4A, showing first and second flow control apparatus coupled to the inflow and outflow vessels for directing fluid flow.

In another embodiment, fluid flow can be switch in only a portion of a body part. For example, fluid flow can be switched in only one or some of the inflow vessels and only one or some of the outflow vessels, and the remaining inflow and outflow vessels of the body part can remain unchanged. This can be achieved by coupling a flow control system to only the inflow and outflow vessels to be switched, and configuring the system such that fluid flow through the remaining inflow and outflow vessels remains unchanged. By way of non-limiting example, FIG. 4A illustrates one method for switching fluid flow into the body part P in only one of the two inflow vessels ViI, Vi2 and one of the two outflow vessels VO1, V02 of FIG. 3A. As shown, fluid flow can be switched by forming a blockage Bi1 in the first inflow vessel ViI and a blockage BO1 in the first outflow vessel VO1, and then redirecting the fluid flow to cause all fluid in the proximal side Pi1 of the first inflow vessel ViI to be delivered to the distal side DO1 of the first outflow vessel VO1, and to cause all fluid in the distal side Di1 of the first inflow vessel ViI to be delivered to the proximal side POI of the first outflow vessel VO1. Unlike with the embodiment in FIG. 3B, the second inflow and outflow vessels Vi2, V02 are not blocked, and thus fluid flow through these vessels remains unchanged. However, fluid flow in the second vessels Vi2, V02 can optionally be switched without forming blockages, and in particular by configuring the flow control system coupled to the first vessels ViI, VO1 to apply enough negative pressure to cause all fluid flowing into and out of the body part P to be switched. As a result of the reversal shown in FIG. 4A, fluid will flow into the body part P from the distal side DO1 of the first fluid outflow vessel VO1, and fluid will flow out of the body part P and into the distal side Di1 of the first fluid inflow vessel ViI, and thus fluid flow is switched in the distal sides Di1, DO1 of the first inflow and outflow vessels ViI, VO1. Fluid flow will remain the same in the proximal sides Pi1, POI of the first inflow and outflow vessels ViI, VO1. FIG. 4B illustrates a switching configuration similar FIG. 4A, except that fluid flow is switched in the second inflow and outflow vessels Vi2, V02, rather than the first inflow and outflow vessels ViI, VO1. Moreover, the second inflow and outflow vessels Vi2, V02 are shown coupled to a flow control apparatus F1 for directing fluid flow, e.g., between the proximal ends of the balloon catheters implanted in the vessels, as previously explained. As further shown in FIG. 4B, a second flow control apparatus F2 can be coupled to the first fluid inflow and outflow vessels ViI, VO1 for performing various tasks, such as drug delivery, dialysis, filtration, pumping, etc.

Figure 5B:
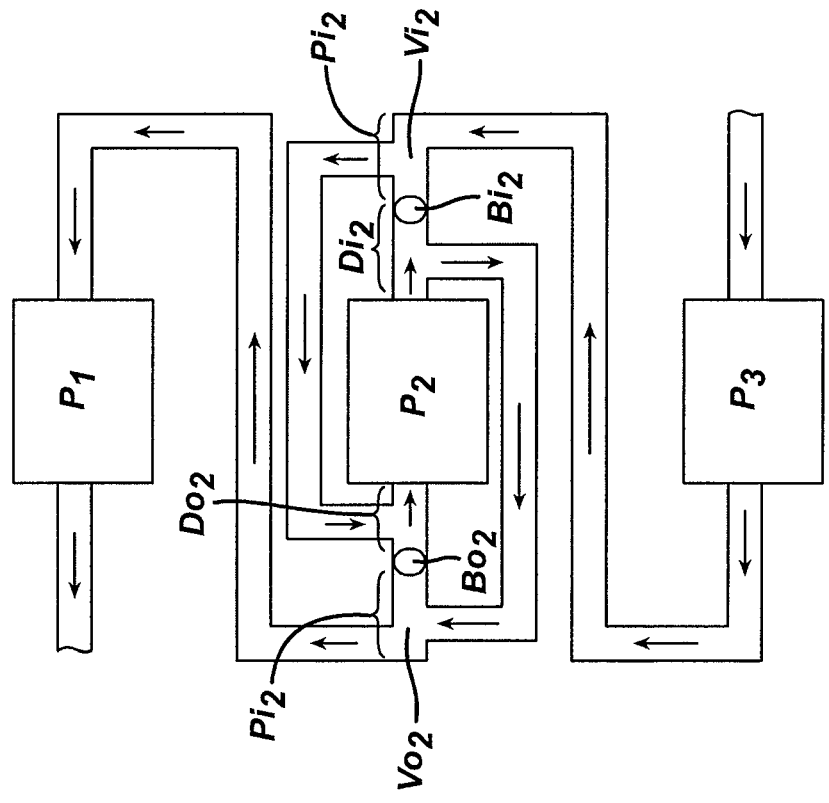
FIG. 5B is a diagram illustrating fluid flow switched in one of the body parts of FIG. 5A while fluid flows in a normal direction in the remaining adjacent body parts.
Figure 5A:
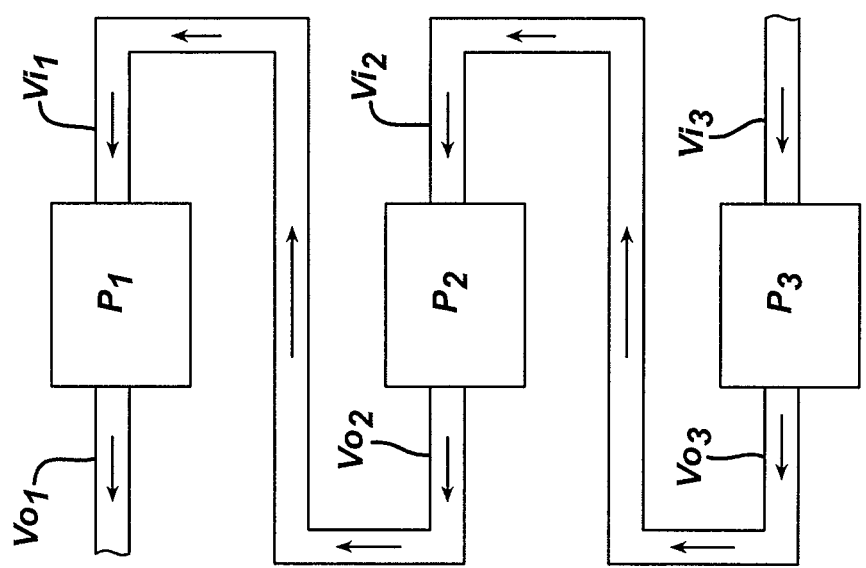
FIG. 5A is a diagram illustrating normal fluid flow through multiple body parts arranged III senes.
Figure 5C:
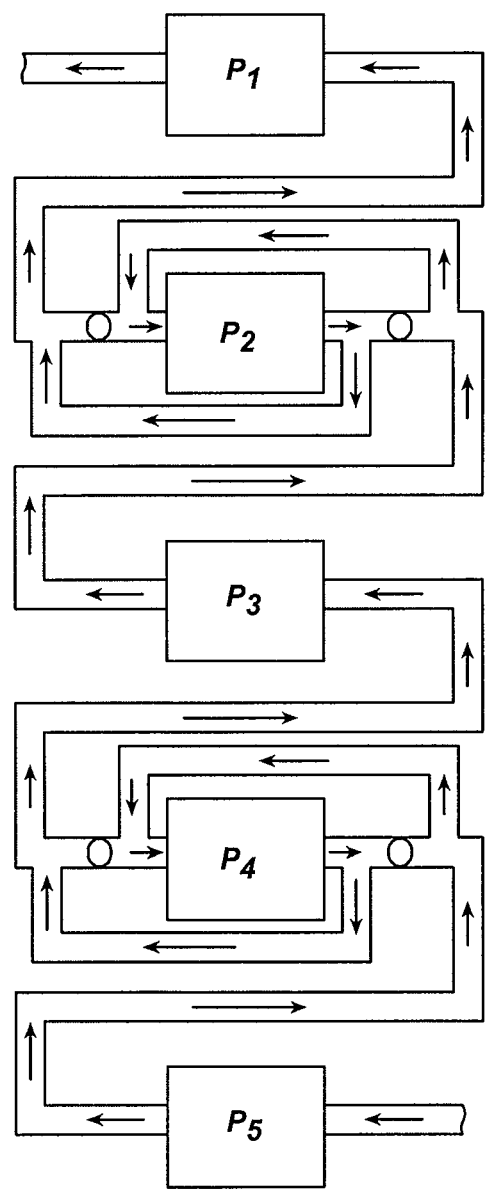
FIG. 5C is a diagram illustrating fluid flow switched in every other body part of FIG. 5A while fluid flows in a normal direction in the remaining adjacent body parts.

Fluid flow can not only be switched for a single body part, but the various methods and devices disclosed herein can also be used to switch fluid flow in one or more adjacent body parts, i.e., body parts arranged in series with one another. FIG. 5A illustrates a series of body parts PI, P2, P3, each having an inflow vessel ViI, Vi2, Vh and an outflow vessel VO1, V02, V03. Since the body parts PI, P2, P3 are arranged in series, the outflow vessel of one body part will also be the inflow vessel of the adjacent body part. As shown in FIG. 5B, fluid flow is switched in the second body P2 part only, and fluid flow remains unchanged (i.e., normal flow direction) in the first and second body parts PI, P3. The techniques discussed above can be used to switch fluid flow in the second body part P2, i.e., by directing fluid from a proximal side Pi2 of a blockage Bi2 in the inflow vessel Vi2 to a distal side Di2 of a blockage B02 in the outflow vessel V02, and directing fluid from a distal side Di2 of the blockage Bi2 in the inflow vessel Vi2 to a proximal side Pi2 of the blockage B02 in the outflow vessel V02. Since fluid flow remains the same on the proximal sides Pi2, P02 of the blockages Bi2, B02, fluid flow likewise remains unchanged and normal in the adjacent first and third body parts PI, P3. FIG. 5C illustrates a similar configuration in which every other body part in a series of body parts has the flow switched. In particular, five body parts PI, P2, P3, P4, Ps are shown in series, and the flow is switched in the second and fourth body parts P2, P 4. The flow remains normal in the first, third, and fifth body parts PI, P3, Ps.

Figure 6A:
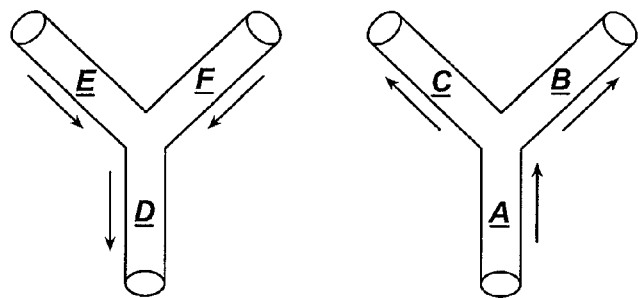
FIG. 6A is a diagram illustrating normal fluid flow through a bifurcated fluid inflow vessel and a bifurcated fluid outflow vessel.

Similar flow switching techniques can also be applied to vessel junctions, such as a vessel that is bifurcated to have a Y-shaped configuration. FIG. 6A illustrates a bifurcated fluid inflow vessel having three segments A, B, C, and a bifurcated fluid outflow vessel having three segments D, E, F. As indicated by the arrows, fluid in the inflow vessel normally flows from segment A to segments B and C, and fluid in the outflow vessel normally flows from segments E and F to segment D. Anyone or more of the three fluid inflow vessel segments and/or fluid outflow vessel segments can be switched to flow in a direction opposite to the normal fluid flow direction, thus switching flow for at least a portion of a body part coupled thereto. Moreover, distinct portions of any of the vessel segments can also or alternatively be switched. By way of non-limiting example, FIGS. 6B-6E illustrate various configurations for switching fluid flow at a vessel junction.

Figure 6B:
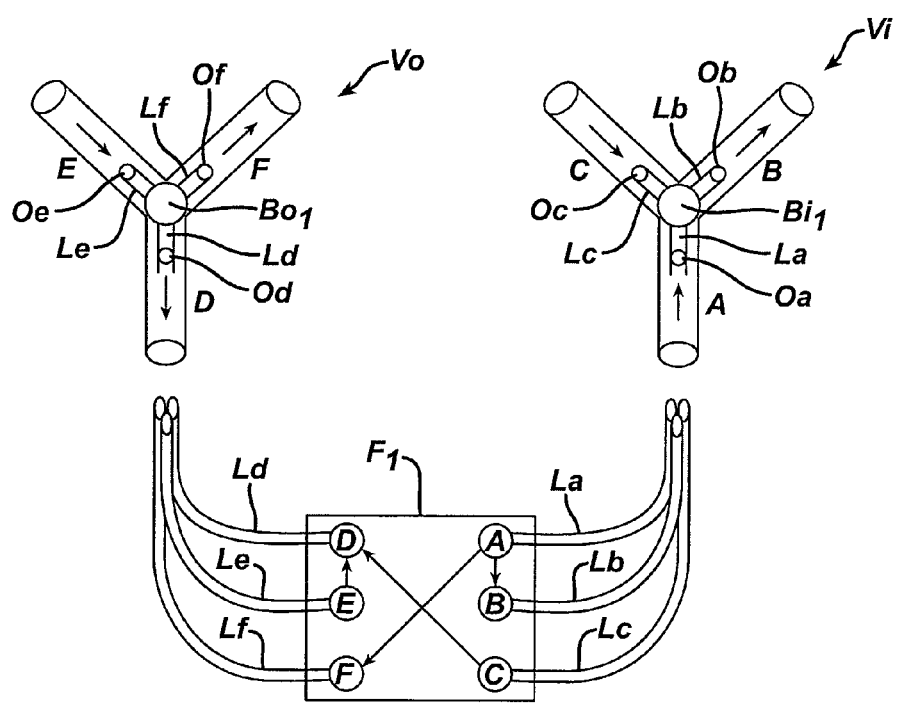
FIG. 6B is a diagram illustrating fluid flow switched in one of the segments of the fluid inflow vessel and one of the segments of the fluid outflow vessel of FIG. 6A.

FIG. 6B illustrates fluid flow being switched in inflow vessel segment C and outflow vessel segment F. As shown, a first blockage Bi1 is formed at the junction of the fluid inflow vessel Vi such that all fluid flow between segments A, B, and C is blocked, and likewise a second blockage B01 is formed at the junction of the fluid outflow vessel Vo such that all fluid flow between segments D, E, and F is blocked. As explained above, each blockage Bi1, B01 can be formed using a balloon catheter. In this embodiment, however, where the inflow and outflow vessels Vi, Vo each include three segments, each balloon catheter preferably has three lumens extending therethrough (in addition to an inflation lumen for inflating the expandable balloon). FIG. 6B illustrates three tubular members La, Lb, Lc in the fluid inflow vessel Vi and three tubular members Ld, Le, Lf in the fluid outflow vessel Vo. Two of the three lumens on each balloon catheter can include a distal end with an opening that is positioned distal of the expandable balloon, and the other lumen can include a distal end with an opening that is positioned proximal to the expandable balloon. As shown in FIG. 6B, tubular member La has an opening Oa that is positioned proximal to the expandable balloon that forms blockage Bi1 in the inflow vessel Vi, and tubular members Lb and Lc each have an opening ~b, Oc that is positioned distal to the expandable balloon that forms blockage Bi1. Similarly, tubular member Ld has an opening Od that is positioned proximal to the expandable balloon that forms blockage B01 in the outflow vessel Vo, and tubular members Le and Lf each have an opening Oe, Of that is positioned distal to the expandable balloon that forms blockage Bo1. As a result, the lumen in tubular member La is in fluid communication with the vessel segment A, the lumen in tubular member Lb is in fluid communication with the vessel segment B, the lumen in tubular member Lc is in fluid communication with vessel segment C, the lumen in tubular member Ld is in fluid communication with vessel segment D, the lumen in tubular member Le is in fluid communication with vessel segment E, and the lumen in tubular member Lf is in fluid communication with vessel segment F.

A flow control apparatus F1 can be coupled to and in fluid communication with the proximal end of each tubular member La, Lb, Lc in the balloon catheter implanted in the inflow vessel Vi and with the proximal end of each tubular member Ld, Le, Lf in the balloon catheter implanted in the outflow vessel Vo. The flow control apparatus F1 can thus direct fluid flow between the various proximal ends to achieve the desired switching. In the embodiment shown in FIG. 6B, as indicated above fluid flow is switched in inflow vessel segment C and outflow vessel segment F. This is achieved by directing all fluid flow received through tubular member La from vessel segment A to both tubular member Lf which delivers the fluid to vessel segment F and to tubular member Lb which delivers the fluid to vessel segment B. All fluid flow received through tubular member Lc from vessel segment C can also be directed and delivered to tubular member Ld which delivers the fluid to vessel segment D. Fluid flowing into tubular member Le from segment E can also be directed and delivered to tubular member Ld which delivers fluid to vessel segment D. As a result of fluid from segment A being delivered to segment F and fluid from segment C being delivered to segment D, the fluid flow through segments F and C is switched.

Figure 6C:
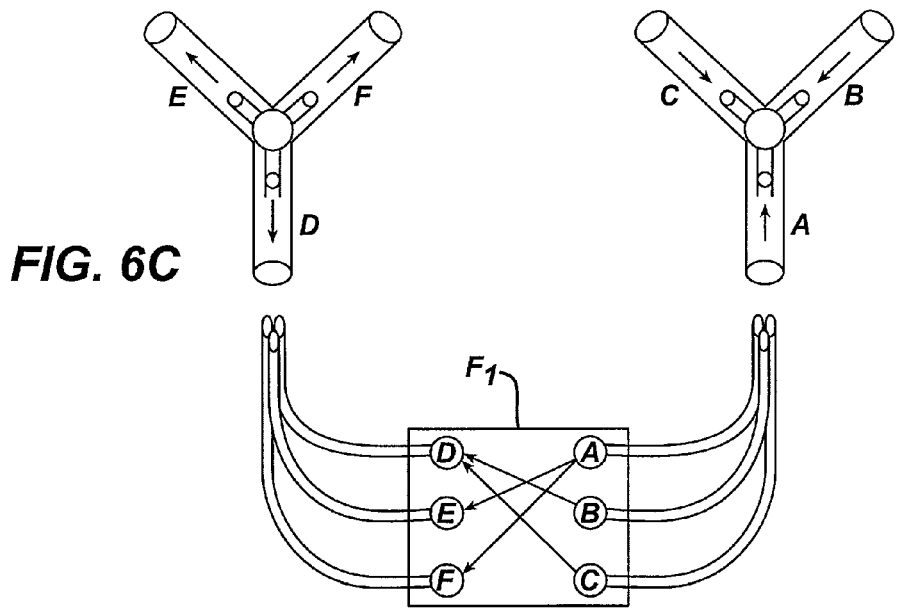
FIG. 6C is a diagram illustrating fluid flow switched in two of the segments of the fluid inflow vessel and two of the segments of the fluid outflow vessel of FIG. 6A.

FIG. 6C illustrates another configuration in which the fluid flow is switched in segments B, C, E, and F. In this embodiment, all fluid flow received through tubular member La from vessel segment A is directed and delivered to both tubular member Le which delivers the fluid to vessel segment E and to tubular member Lf which delivers the fluid to vessel segment F. All fluid flow received through tubular member Lb from vessel segment B and all fluid flow received through tubular member Lc from vessel segment C is directed and delivered to tubular member Ld which delivers the fluid to vessel segment D. As a result of fluid from segment A being delivered to segments E and F and fluid from segments B and C being delivered to segment D, the fluid flow through segments B, C, E, and F is switched.

Figure 6D:
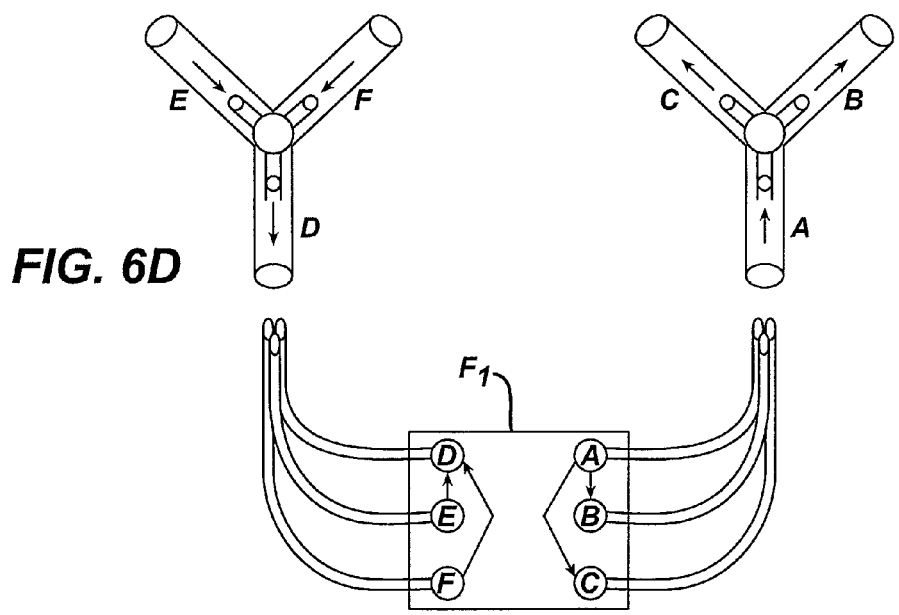
FIG. 6D is a diagram illustrating fluid flow switched in all three of the segments of the fluid inflow vessel and all three of the segments of the fluid outflow vessel of FIG. 6A.

In another configuration, shown in FIG. 6D, rather than switching fluid flow, the fluid is delivered from segment A, through tubular member La to segments B and C, through tubular members Lb and Lc, and from segments E and F, through tubular members Le and Lf, to segment D, through tubular member Ld, in its normal direction. In this embodiment, while fluid flow is not switched, the flow control system can be used to avoid a naturally-occurring blockage formed in the vessel(s) due to deterioration of the vessel, and/or to manipulate the pressure-flow relationship to alter the wave dynamics of fluid inside the vessels. Such a configuration can be particularly useful in the extremities, for example where circulation is poor due to diabetes or other conditions.

Figure 6E:
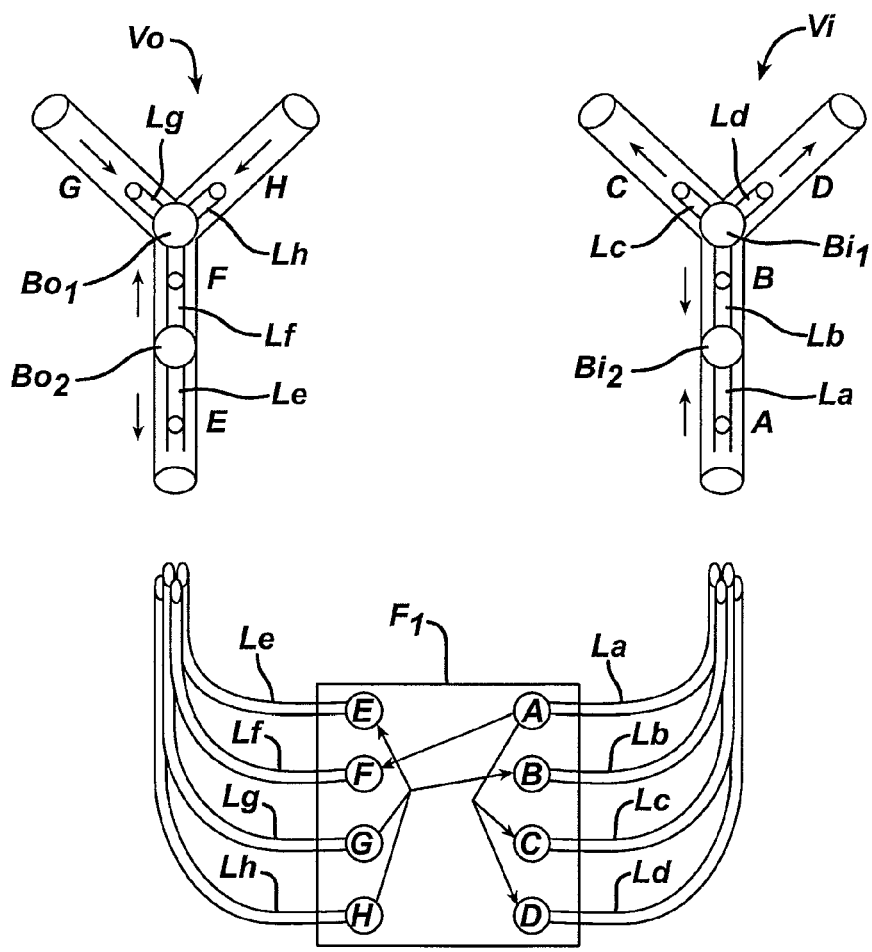
FIG. 6E is a diagram illustrating fluid flow switched in a portion of one of the segments of the fluid inflow vessel and a portion of one of the segments of the fluid outflow vessel of FIG. 6A.

FIG. 6E illustrates another embodiment of a configuration for switching fluid flow in inflow and outflow vessels that are bifurcated. In this embodiment, each balloon catheter has two expandable members for forming first and second blockages. In particular, as shown the inflow vessel Vi includes a first blockage Bi1 at the junction and a second blockage Bi2 located in one of the segments. As a result of the second blockage Bi2, one of the segments is separated into segments A and B. The remaining two segments that extend from the junction are referred to as segments C and D. Similarly, the outflow vessel Vo includes a first blockage B01 at the junction and a second blockage B02 located in segment D, and as a result of the second blockage B02, one of the segments is separated into segments E and F. The remaining two segments that extend from the junction are referred to as segments G and H. The balloon catheter in the inflow vessel Vi thus includes four tubular members La, Lb, Lc, Ld, each having an open distal end in fluid communication with a segment A, B, C, D, respectively, and the balloon catheter in the outflow vessel Vo includes four tubular members Le, Lf, Lg, Lh, each having an open distal end in fluid communication with a segment E, F, G, H, respectively.

As with the previous embodiments, a flow control apparatus F1 can be coupled to and in fluid communication with the proximal end of each tubular member La, Lb, Lc, Ld in the balloon catheter implanted in the inflow vessel Vi and with the proximal end of each tubular member Le, Lf, Lg, Lh in the balloon catheter implanted in the outflow vessel Vo. The flow control apparatus F1 can thus direct fluid flow between the various proximal ends to achieve the desired switching. In the illustrated embodiment, all fluid flow received through tubular member La from vessel segment A can be redirected and delivered to tubular members Lc, Ld, and Lf which deliver fluid to vessel segments C, D, and F respectively. Fluid flowing into tubular members Lg and Lh from segments G and H can be directed and delivered to tubular member Lb which delivers to vessel segment B and to tubular member Le which delivers fluid to vessel segment E. As a result, fluid flow through segments B and F is switched, while fluid flow remains normal through remaining segments A, C, D, E, G, and H. Such a configuration can be particularly useful in cases of local obstruction to an organ or a limb along the long axis of a blood vessel while the rest of the organs supplied by the vessel are intact. It also obviates the need to do a total flow reversal in a long vessel, such as the aorta, if one side (e.g., the left) of the organ or limb is affected while the other side (e.g., the right) is intact (partial reversal or unilateral reversal). Such a switching configuration is also useful in the situation of a segment of aortic dissection, wherein the switch in segments B and F can create a low pressure system preventing further dissection.

A person skilled in the art will appreciate that the various switching configurations set forth in FIGS. 2A-6E can be applied to various body parts. FIGS. 7A-12 illustrate various exemplary applications.

Turning first to FIG. 7A, one exemplary technique for switching fluid flow through the brain is shown. In this embodiment, oxygenated blood flow is switched through the cerebrovascular system, i.e., arterial-venous switching is achieved. This is particularly advantageous for treating acute stoke, as the venous blood supply system is used as an alternative pathway for perfusing the brain with oxygenated blood. The use of arterial-venous switching is also advantageous as the particular location of the clot is irrelevant, and the switching can be used to treat both ischemic and hemorrhagic strokes.

In general, as shown in a schematic representation of the brain in FIG. 7A, during normal blood flow oxygenated blood is delivered to the brain from the heart through an inflow vessel, i.e., the carotid arteries, namely the left and right internal carotid arteries LICA, RICA, which branch into the left anterior cerebral artery LACA and the left middle cerebral artery LMCA and the right anterior cerebral artery RACA and the right middle cerebral artery RMCA, respectively, and through the left and right posterior arteries LP, RP. The blood exits the brain through an outflow vessel, namely the right and left internal jugular veins LI1, RI1. In order to switch blood flow through the brain such that blood is delivered to the brain through the outflow vessel and blood is drained from the brain through the inflow vessel, one or more balloon catheters can be implanted in each of the inflow and outflow vessels to form one or more blockages. The particular quantity and location of the blockages can vary. For example, in one embodiment a blockage can be formed in only one of the inflow arteries that deliver blood into the brain. As indicated above, a flow control apparatus coupled to the catheter forming the blockage can be used to apply a negative pressure that is effective to switch blood flow through any number of the arteries. In an exemplary embodiment, however, a first flow control apparatus having a first catheter used to form blockages in the left internal carotid arteries and a second catheter used to form blockages in the left internal jugular vein is provided, and a second flow control apparatus having a first catheter used to form blockages in the right internal carotid arteries and a second catheter used to form blockages in the right internal jugular vein is provided. Thus, while the following techniques only illustrate one flow control system coupled to one of the left and/or right side of the brain, a similar flow control system can likewise be coupled to the opposite side of the brain. As a result of using two flow control systems coupled to both the left and right sides of the brain, a negative pressure can be generated in both the left and right middle and anterior carotid arteries that is sufficient to overcome the positive pressure normally produced by blood flow into the brain from the left and right posterior arteries, thereby causing all blood flow in the left and right anterior, middle, and posterior arteries to be switched and to flow in an opposite direction such that blood will drain from the brain into the arteries, and blood will flow into the brain from the veins.

Figure 7B:
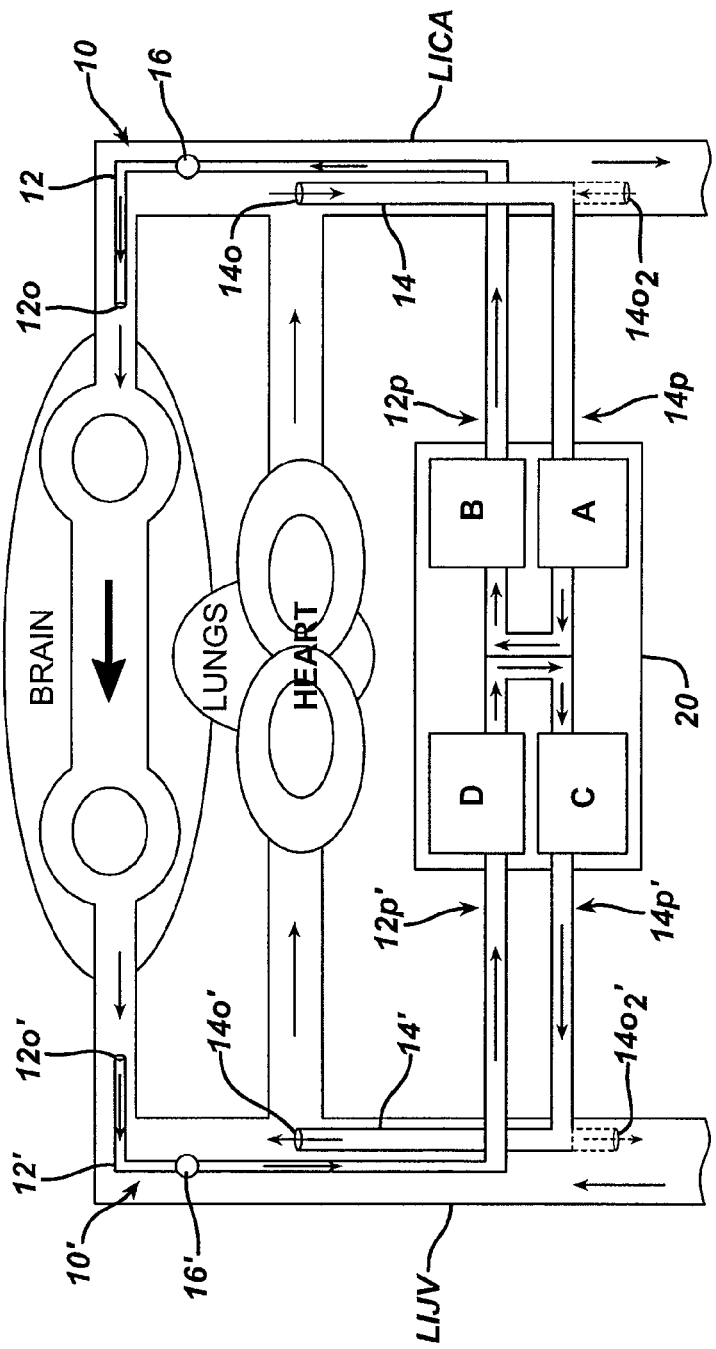
FIG. 7B is a diagram illustrating a flow control system implanted in the arterial and venous vessels of the brain with blood flowing in the normal direction.

Such a configuration is illustrated in more detail in FIG. 7B. A person skilled in the art will appreciate that, while FIG. 7B only illustrates one catheter implanted in the left internal carotid artery LICA and one catheter implanted in the left internal jugular vein LIJV, a catheter can also optionally be implanted in the right internal carotid artery and another in the right internal jugular vein. Moreover, while FIG. 7B illustrates the catheters 10, 10' of FIG. 1, each catheter can have a variety of other configurations. As shown, the first catheter 10 is implanted in the artery such that the balloon 16, in a deflated configuration, is positioned between a first opening 120 extending into the lumen in the first tubular member 12 of the catheter 10 and a second opening 140 extending into the lumen in the second tubular member 14 of the catheter 10. The second catheter 10' is likewise implanted in the vein such that the balloon 16', in a deflated configuration, is positioned between a first opening 120' extending into the lumen in the first tubular member 12' of the catheter 10' and a second opening 140' extending into the lumen in the second tubular member 14' of the catheter 10'. In an exemplary embodiment, the first and second catheters 10, 10' are introduced through the femoral artery and femoral vein using known techniques. The distal end of the catheter 10 inserted through the femoral artery is preferably positioned in the ipsilateral carotid artery, and the distal end of the catheter 10' inserted through the femoral vein is preferably positioned to sit within the internal jugular vein, through a valve separating the distal internal jugular vein from the right atrium.

The proximal end 12*p*, 14*p*, 12*p'*, 14*p'* of each tubular member 12, 14, 12', 14' is coupled to a flow control apparatus 20 which is effective to control the direction of blood flow between the tubular members 12, 14, 12', 14' of each catheter 10, 10'. In this configuration, since the balloons 16, 16' have not yet been inflated to block blood flow through the artery LICA and the vein LIN, the flow control apparatus 20 can direct blood flow along its normal pathway. In particular, the flow control apparatus 20 can direct blood flowing from the heart and into the opening 140 in the second tubular member 14 and out of the proximal end 14*p* into the proximal end 12*p* of the first tubular member 12, which delivers the blood out of the opening 120 and into the brain. Likewise, the flow control apparatus 20 can direct blood flowing from the brain and into the opening 120' in the first tubular member 12' and out of the proximal end 12*p'* into the proximal end 14*p'* of the second tubular member 14', which delivers the blood out of the opening 140' and to the heart. FIG. 7B illustrates four pumps A, B, C, D located in the flow control apparatus 20, with pump A coupled to tubular member 12, pump B coupled to tubular member 14, pump C coupled to tubular member 12', and pump D coupled to tubular member 14'. As shown, pumps A and B are coupled such that blood can flow from A to B, and pumps C and D are coupled such that blood can flow from D to C. A person skilled in the art will appreciate that, while the term pump is used, elements A, B, C, and D can have any configuration and they can merely be pathways for receiving blood flow therethrough, or they can include any number of features to facilitate the flow of blood, such as a valve, a flow control mechanism for controlling a rate of blood flow therethrough, a drug delivery apparatus, a dialysis unit, etc.

Figure 7C:
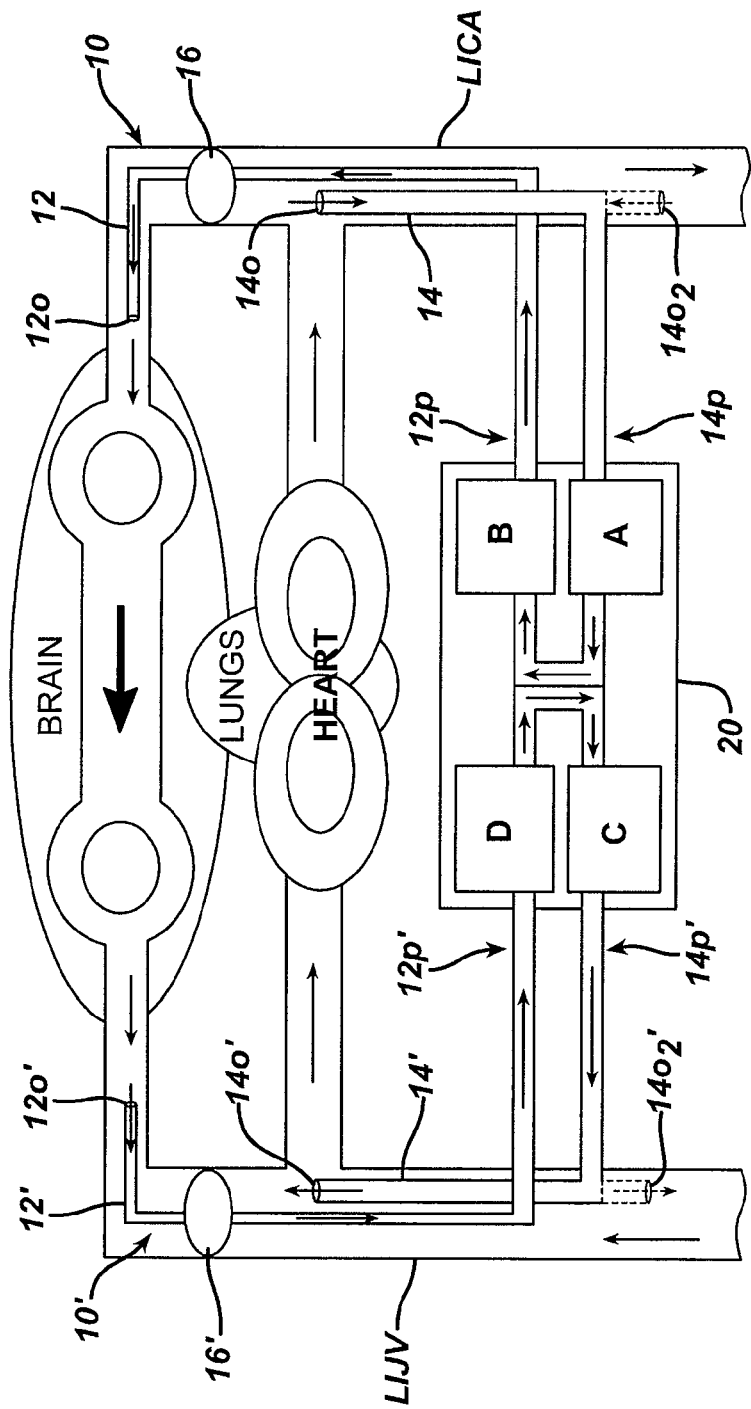
FIG. 7C is a diagram illustrating first and second balloons of the flow control system expanded to form blockages, with blood still flowing in the normal direction.

Once blood flow through the flow control apparatus 20 is established, the balloons 16, 16' can be inflated to block all blood flow between proximal and distal sides thereof, as shown in FIG. 7C. Blood continues to flow in the natural direction in this configuration, as explained above with respect to FIG. 7B.

Once the blockages are formed by the balloons 16, 16', blood flow can be switched by switching the coupling in the flow control apparatus 20. In particular, as shown in FIG. 7D, the coupling between the pumps A, B, C, D can be switched such that blood in pump A is delivered to pump D and blood in pump B is delivered to pump C. As a result, blood will flow from the heart into the left internal carotid artery LICA (i.e., in the inflow side), where it will flow into the opening 140 in the distal end of the second tubular member 14 since it is blocked by the balloon 16 from flowing into the brain. The blood will flow from the proximal end 14*p* of the tubular member 14 and into pump A, wherein it is redirected to pump D which delivers the blood to the first tubular member 12' in the left internal jugular vein LI1V (i.e., in the outflow side). The blood will pass through the first tubular member 12' and will flow out of the opening 120' in the proximal end of the tubular member 12'. Since it is blocked by the balloon 16' from flowing in its normal direction to the heart, the blood will flow into the brain. The blood exiting the brain will then enter the opening 120 in the proximal end of the first tubular member 12 in the left internal carotid artery LICA, since it is blocked from flowing to the heart by the balloon 16. The blood flowing through the first tubular member 12 will be delivered to pump B, where it is redirected and delivered to pump C, which is coupled to the proximal end 14*p'* of the second tubular member 14' in the left internal jugular vein LIN. The blood flowing through the second tubular member 14' will exit the opening 140' in the distal end thereof, where it can flow to the heart since it is blocked by the balloon 16' from flowing to the brain. The blood will therefore recirculate through the brain in a direction opposite to normal, i.e., blood is delivered through the venous vessels and blood exits the brain through the arterial vessels. All blood flow located on the proximal side of the blockage (i.e., that is blocked from fluid communication with the brain) in the left internal jugular vein LI1V (as well as the right, not shown) and the left internal carotid artery LICA (as well as the right, not shown) will continue to flow in its normal direction.

As further shown in FIGS. 7B-7D, the second tubular members 14, 14' can also optionally includes a second opening 1402, 1402' that is located near or within the femoral artery and the aortic arch (or toward femoral vein), respectively. The second openings 1402, 1402' can be used to help regulate the blood pressure, as too much blood removed from the heart can result in a low blood pressure and vice versa. By adding the opening 1402 in second tubular member 14, additional blood can optionally flow into the second tubular member 14 from the femoral artery to supplement the blood received from the heart, thus requiring less blood from the heart. Similarly, blood can drain through the additional opening 1402' in second tubular member 14' to decrease the amount of blood added into the heart.

Figure 8A:
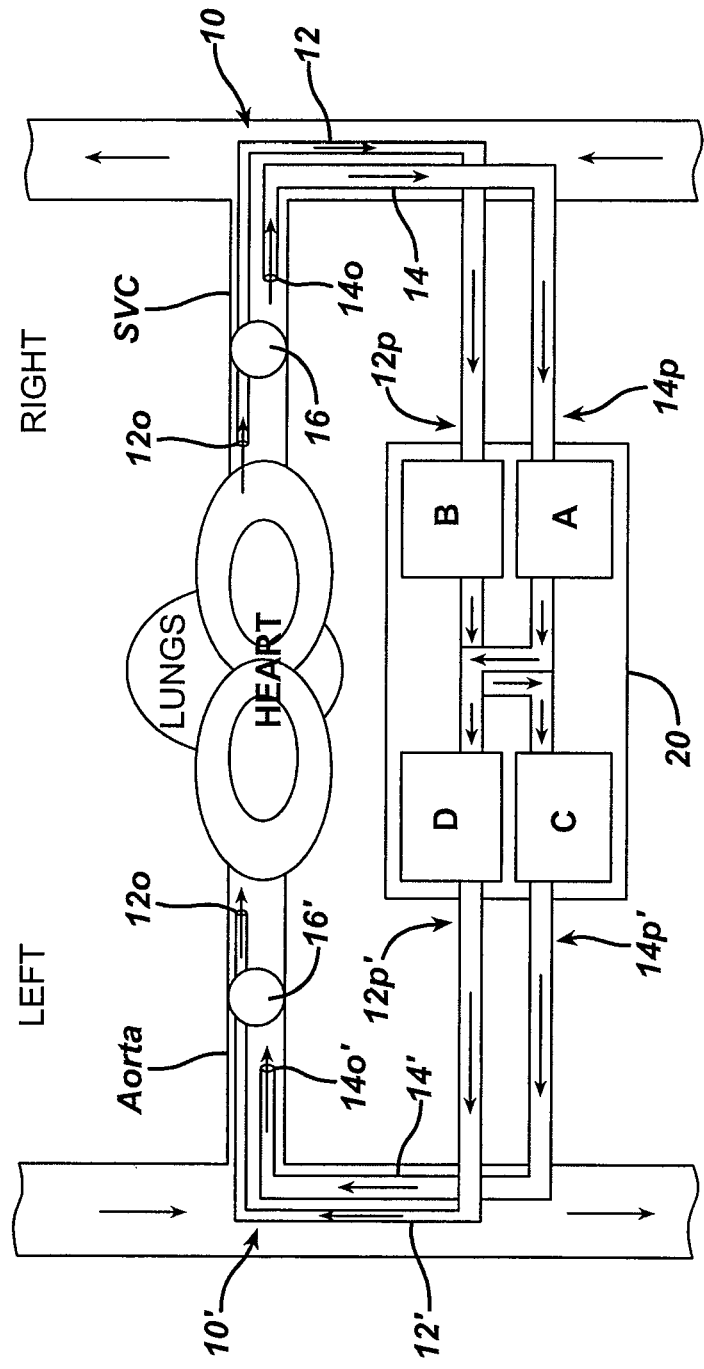
FIG. 8A is a diagram illustrating the pumping mechanism of the heart switched such that blood is pumped from the left side of the heart to the right side of the heart.

In another embodiment, shown in FIG. 8A, a similar configuration can be applied to the heart to switch the left and right pumping mechanisms of the heart. Switching the heart will likewise switch the lungs. In general, blood enters the right atrium of the heart through the inferior and superior vena cava, flows to the lungs through the pulmonary artery, and then the pulmonary vein empties blood from the lungs into the left atrium where the blood is delivered to the aorta. Blockages can be formed in both the superior vena cava and inferior vena cava on the right side of the heart and the aorta on the left side of the heart. While FIG. 8A illustrates only one blockage formed on the left side of the heart, e.g., in the superior vena cava SVC, another catheter can be provided for forming a blockage in the inferior vena cava. The flow through the inferior vena cava can mimic the flow through the superior vena cava. As shown in FIG. 8A, a first catheter 10 can be implanted in the superior vena cava SVC to form a first blockage using the balloon 16 disposed thereon. As a result, an opening 120 in the distal end of the first tubular member 12 will be in fluid communication with the heart, and an opening 140 in the distal end of the second tubular member 14 will be blocked from communication with the heart. Likewise, a second catheter 10' can be implanted in the aorta to form a second blockage using the balloon 16' disposed thereon. As a result, an opening 120' in the distal end of the first tubular member 12' will be in fluid communication with the heart, and an opening 140' in the distal end of the second tubular member 14' will be blocked from communication with the heart. The proximal ends 12*p*, 14*p*, 12*p'*, 14*p'* of the first and second catheters 10, 10' can be coupled to a flow control apparatus 20, as previously discussed with respect to FIGS. 7B-7D, such that blood flow through the heart can be switched. In particular, blood that is normally delivered to the right side of the heart from the superior vena cava SVC is blocked from flowing into the heart, and instead flows into the opening 140 in the distal end of the second tubular member 14. The blood will flow through tubular member 14 to pump A, where it is redirected to pump D which is coupled to the first tubular member 12' on the left side of the heart. The blood will then flow out of the opening 120' in the distal end of the first tubular member 12', where it is forced to flow into the left side of the heart in a direction opposite to normal flow due to the blockage by the balloon 16'. Blood exiting the heart through the aorta will flow into the opening 120 in the distal end of the first tubular member 12 on the right side, where it will be delivered to pump B. Pump B redirects the blood to pump C, which is coupled to the second tubular member 14' on the left side of the heart. The blood will exit the opening 140' in the distal end of the second tubular member 14', and is blocked from flowing into the heart and thus flows in its normal direction to the body. Accordingly, blood flow through the heart (and thus the lungs) is completely switched, while blood through the remainder of the body is unchanged. A person skilled in the art will appreciate that certain modifications to the valves in the heart may be necessary to allow for arterial-venous switching of the heart.

Figure 8B:
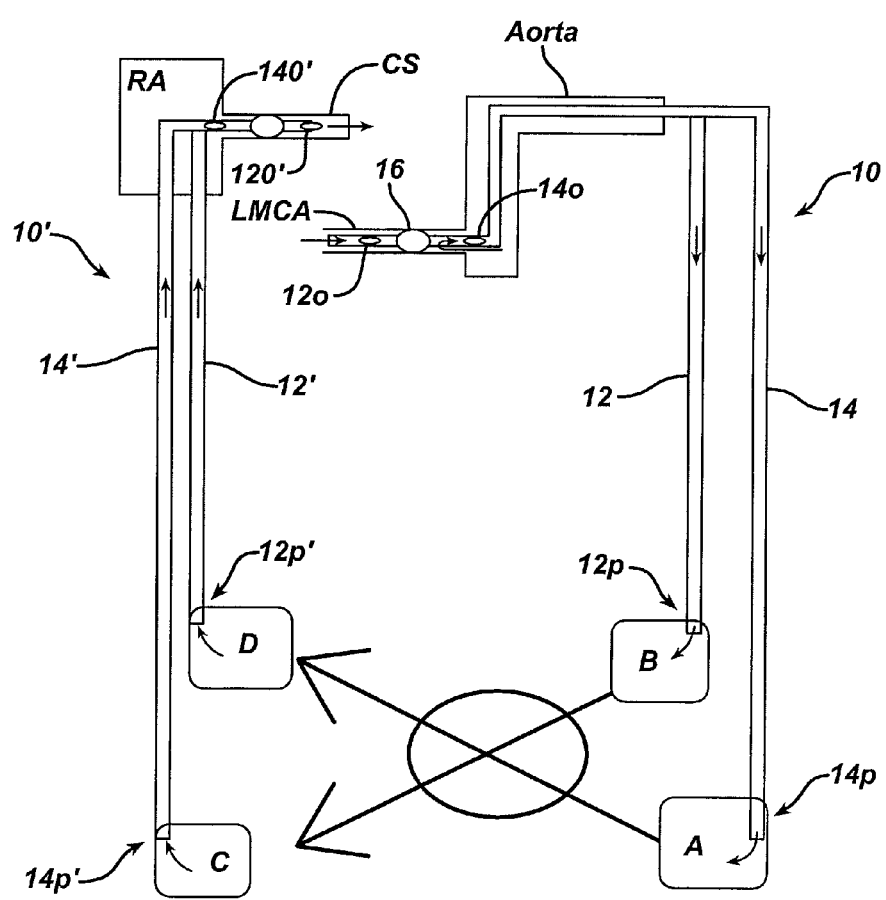
FIG. 8B is a diagram illustrating the coronary circulation system switched such that blood is delivered to the heart through the coronary sinus and exits the heart through the coronary arteries.

In another embodiment, rather than switching the pumping system of the heart, the blood supply to the heart can be switched. In general, blood from the aorta is delivered to the left main coronary artery and the right coronary artery, which deliver oxygen-rich blood to the heart. Oxygen-poor blood exits the heart through the coronary veins, which drain into the coronary sinus. FIG. 8B illustrates one embodiment of a technique for reversing the circulation system of the heart such that blood is supplied to the heart through the coronary sinus and blood exits the heart through the coronary arteries. In particular, as shown in FIG. 8B a first catheter 10 is implanted in the aorta such that the balloon 16 forms a blockage between the aorta and the left main coronary artery. A first opening 120 is located in the left main coronary artery LMCA on a distal side of the balloon 16 such that the first opening 120 is in fluid communication with the heart. A second opening 140 is located in the aorta on a proximal side of the balloon such that the second opening 140 is blocked from fluid communication with the heart. While not shown, another catheter can optionally likewise be implanted in the right coronary artery, and flow through the right coronary artery can mimic flow the flow through the left main coronary artery, as explained below. As further shown in FIG. 8B, a second catheter 10' is implanted in the coronary sinus such that the balloon 16' forms a blockage between a first opening 120' located on a proximal side of the balloon 16' and in communication with the heart and a second opening 140' located on a distal side of the balloon 16' and blocked from communication with the heart. The proximal ends 12p, 14p, 12p', 14p' of the tubular members 12, 14, 12', 14' of each catheter 10, 10' can be coupled to a flow control apparatus 20 which is effective to control the direction of blood flow between the tubular members 12, 14, 12', 14' of each catheter 10, 10'.

In order to switch blood flow, blood normally flowing toward the heart from the aorta will be blocked by the balloon 16 on the first catheter 10, and thus will flow into the second opening 140 and through the second tubular member 14 of the first catheter 10. The flow control apparatus can direct this blood to the first tubular member 14' of the second catheter 10', where it will flow out of the first opening 120' to be delivered to the coronary sinus. Since the balloon 16' on the second catheter 10' forms a blockage, the blood is forced to be delivered to the heart through the coronary sinus. The blood thus flows through the coronary sinus in a direction opposite to normal flow. Once the blood passes through the veins to the arteries in the heart, the blood will flow into the left main coronary artery. The blockage formed by the balloon 16 on the first catheter 10 will force the blood to flow into the first opening 120 in the first tubular member 12 of the first catheter 12. The flow control system 20 will redirect and deliver this blood to the second tubular member 14' of the second catheter 10' and out of the second opening 140', where the blood will flow in its normal direction to the right atrium.

Figure 8C:
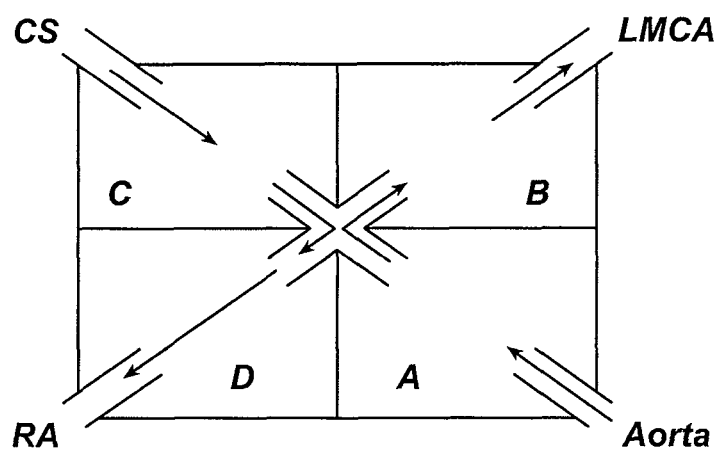
FIG. 8C is a diagram illustrating another technique for switching the coronary circulation system showing a hub made from the left atrial appendage with blood flowing in the normal direction.
Figure 8D:
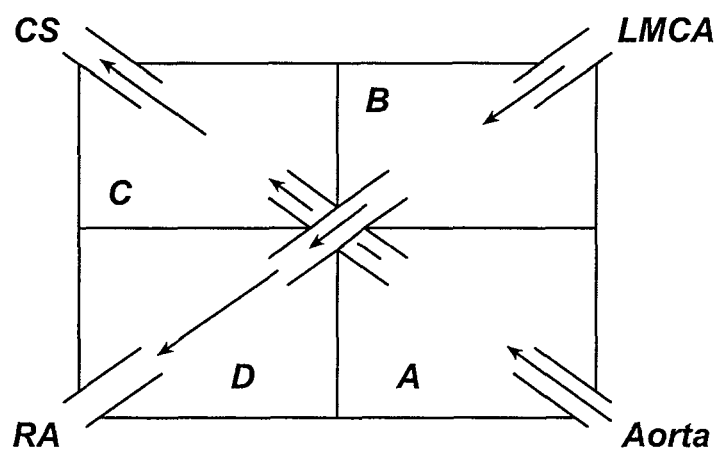
FIG. 8D is a diagram illustrating the system of FIG. 8C showing blood flow switched.

In another embodiment, shown in FIGS. 8C-8D, the left atrial appendage can be used to redirect blood flow through the heart. For example, after disconnecting the left atrial appendage from the left atrium, the appendage can act as a central hub that connects to the left main coronary artery, the aorta, the right atrium, and the coronary sinus. The hub can be formed by implanting a flow control apparatus in the left atrial appendage or using a plurality of catheters or other connects for forming the various connections. During normal flow, as shown in FIG. 8C, a first catheter, located in section A, receives blood from the aorta and the blood is redirected into section B, which delivers blood to the left main coronary artery. From the coronary arteries, blood collects into the coronary veins and then into the coronary sinus, where it is delivered to section C. A third catheter collects blood from section C, and the hub redirects the blood from section C to section D, which delivers blood through a fourth catheter to the right atrium. When flow is switched, as shown in FIG. 8D, blood flows from the aorta to section A, where it is redirected to section C, which delivers blood in a switched direction into the coronary sinus. The coronary sinus distributes the oxygenated blood to the coronary veins, and then it travels to the coronary arteries as deoxygenated blood, eventually be delivered to the coronary artery and to section B of the hub. The blood from section B is redirected by the hub to section D and into the right atrium. The same reversal system can also be deployed for a partial coronary reversal around a cardiac segment, such as the left ventricle. A person skilled in the art will appreciate that a similar connection can be formed between the aorta and the coronary sinus as well as the left main coronary artery and the right atrium without forming a hub in the left atrial appendage. In particular, a balloon catheter can be implanted in each of the aorta, left main coronary artery, right atrium, and coronary sinus to form blockages therein. Each catheter can have a configuration similar to the catheter shown in FIG. 1, and the openings can be connected through a flow control apparatus such that fluid flow is redirected as shown in FIG. 8D.

Figure 8E:
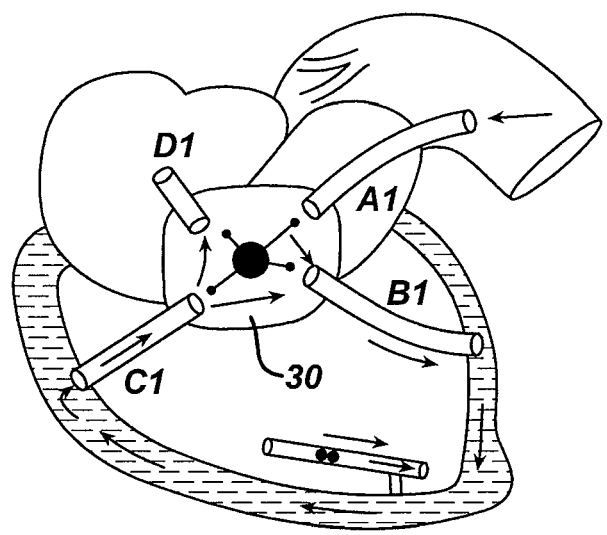
FIG. 8E is a diagram illustrating another technique for switching the coronary circulation system wherein the arterial blood supply is accessed using the pericardial sac.

In another embodiment, shown in FIG. 8E, the pericardial space can be used to access the atrial blood supply and create an alternative arterial network parallel to the original coronary circulation. The hub can connect the new pericardial network to the right atrium after various connection or reperfusion points are created. The pericardium is a very tough tissue that can compress cardiac muscle and cause death due to tamponade before it suffers any damage secondary to increased intra pericardial pressure. The character can be utilized to create a pad of circulating arterial blood around the heart to connect to coronary arteries at various levels. The pericardial blood can be a continuous sac, or divided into compartments following generally the coronary vessels. The sac can be connected to the regulating hub so that it can divert blood into the right atrium to complete the circuit. In particular, both the second and third catheters B1, C1 can be implanted to have an opening in communication with the pericardial sac. Thus, blood will flow from the aorta into the first catheter AI, and then through the hub which directs the blood to the second catheter B1, where it is delivered to the pericardial sac. The blood will then flow through the pericardial space and will enter the third catheter C1, which delivers blood to the hub where it is redirected to the fourth catheter D1 and delivered to the right atrium. The hub can maintain a specific pressure and volume depending on the amount of blood used in each cycle to perfuse the distal coronary vessels.

Figure 8F:
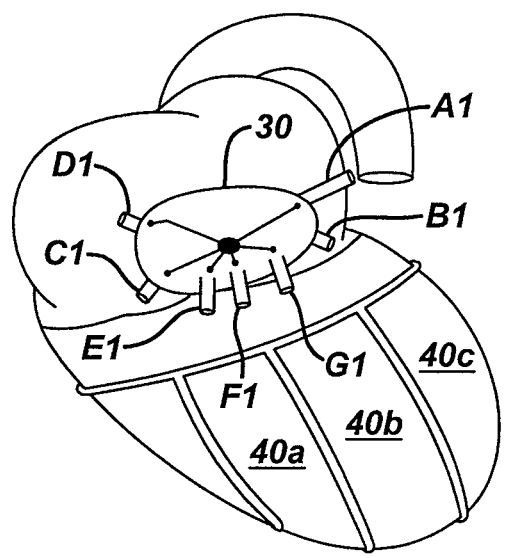
FIG. 8F is a diagram illustrating another technique for switching the coronary circulation system wherein multiple compartments are formed in the pericardial sac for accessing the arterial blood supply.

In yet another embodiment, shown in FIG. 8F, the hub 30 and catheters AI, B1, C1, D1 can be implanted as described above, however the hub can also include one or more additional catheters E1, F1, G1, etc. Each additional catheter can be positioned to be in fluid communication with a compartment 40a, 40b, 40c, etc., created in the pericardial sac, for example using a laser of chemical adhesion. The compartments can follow the main coronary vessels for revascularization. For example, the pericardial sac can be compartmentalized or partitioned to include a transverse partition for the right coronary and circumflex, and to include longitudinal partitions for the left anterior descending, circumflex coronary artery, posterior descending artery, and large diagonal coronary arteries. The hub can regulate pressure in each of the compartments.

Figure 8G:
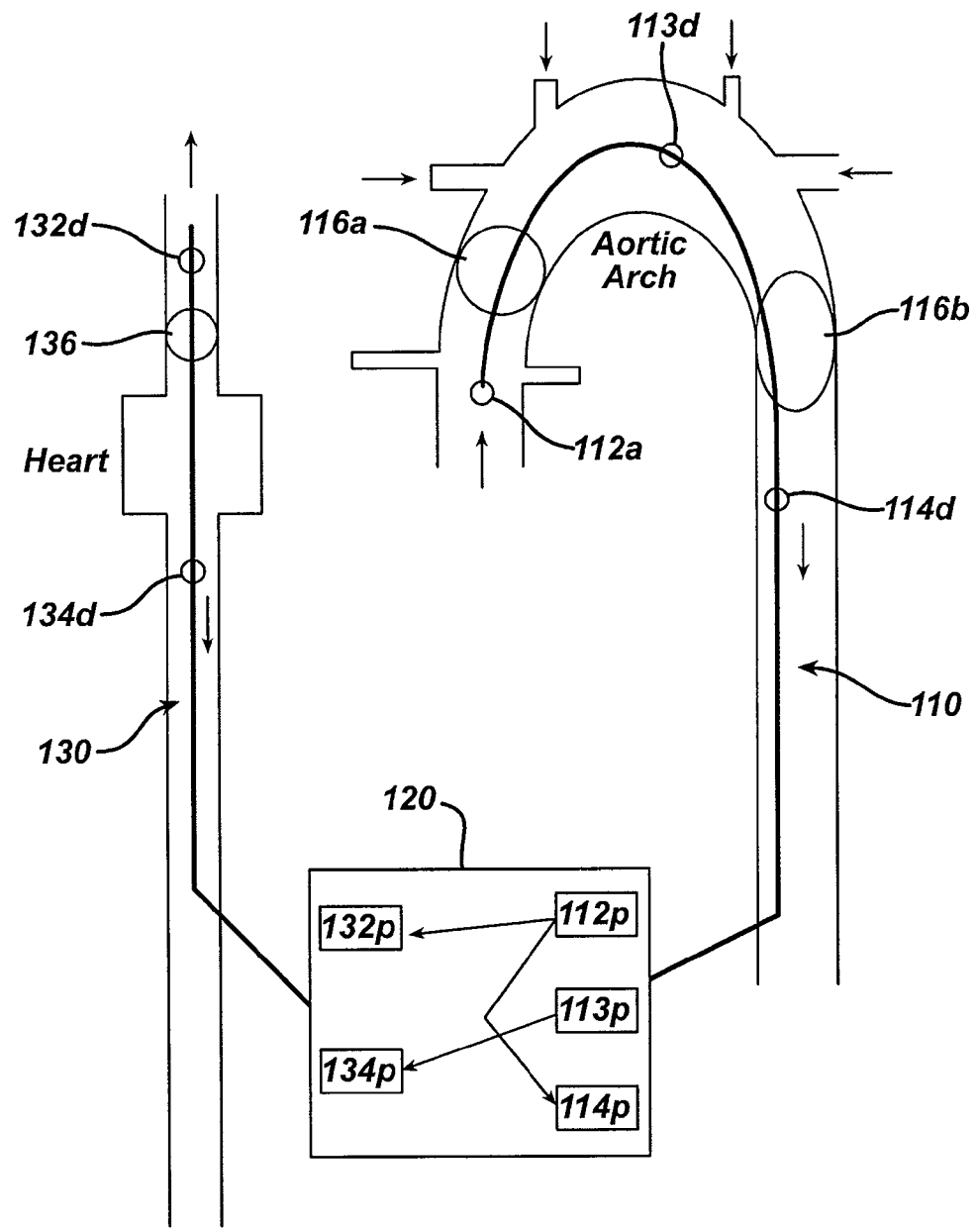
FIG. 8G is a diagram illustrating blood flow switched through the aortic arch.

In yet another embodiment, blood flow through the aortic arch, or through a segment thereof, can be switched. This is particular useful where surgical manipulation of the aortic arch is mandatory, for example in cases of aortic arch replacement. Such manipulations are particularly harmful due to resultant fragmentation of fat emboli into the arterial circulation and the high probability of causing stroke. By creating a switched flow in the aortic arch area where all vessels branch to the brain, the vessels become veins instead of arteries and the blood flow is directed away from the brain into the venous circulation while the brain receives blood from the superior vena cava in an opposite direction. The catheter inside the superior vena cava delivers blood past the valve inside the internal jugular vein while the creation of a low blood pressure chamber on the other side (aortic arch) helps complete the reversal of flow across the cerebral circulation. As shown in FIG. 8G, in this embodiment the flow control system can include two catheters 110, 130 coupled to a flow control apparatus 120. The first catheter 110 can include three lumens (not shown) formed therethrough and each having an open distal end 112d, 113d, 114d for receiving fluid flow therethrough and a proximal end 112p, 113p, 114p (generically illustrated as a box) that is coupled to the flow control apparatus 120. An expandable balloon 116a, 116b can be positioned between each open distal end 112d, 113d, 114d for forming a blockage. As a result, the first distal end 112d will be located distal to the first expandable balloon 116a, the second distal end 113d will be located between the first and second expandable balloons 116a, 116b, and the third distal end 114d will be located proximal to the second expandable balloon 116b. The second catheter 130 can include two tubular members or lumens, each having an open distal end 132d, 134p for receiving fluid flow therethrough and a proximal end 132p, 134p (generically illustrated as a box) that is coupled to the flow control apparatus 120. An expandable balloon 136 can be disposed between the distal ends 132d, 134d.

In use, the first catheter 110 can be inserted into the aortic arch and the balloons 116a, 116b can be positioned on opposite sides of the arch such that the arteries extending from the arch are located between the balloons and in fluid communication with the second open distal end 113d. The second catheter 130 can be inserted through the inferior vena cava and up into the superior vena cava to position the balloon 136 in the superior vena cava. When the balloons are expanded to form blockages and the flow control apparatus 120 is configured to switch blood flow, blood will flow from the left ventricle toward the aortic arch, where it will be blocked by the first balloon 116a. The blood will thus flow into the first open distal end 112d on the first catheter 110 to be delivered to the hub. The hub will direct the blood from the first proximal end 112p to the third proximal end 114p of the first catheter 10 and to the first proximal end 132p of the second catheter 130. Blood flowing into the third proximal end 114p will be delivered to the third distal end 114d, where it will flow in its normal direction. Blood flowing into the first proximal end 132p of the second catheter 130 will be delivered to the second distal end 132d of the second catheter 130, where it will flow in a direction opposite to normal through the superior vena cava to the brain. The blood will then flow out of the brain and through the arteries and into the aortic arch, again in a direction opposite to normal. Since blood flowing from the arteries into the aortic arch is blocked by the first and second balloons 116a, 116b, the blood will flow into the second open distal end 113d, where it will be delivered to the hub 120 via the second proximal end 113p. The hub 120 will direct the blood from the second proximal end 113p of the first catheter 110 to the second proximal end 134p of the second catheter 130, where it will flow out of the second distal end 134d of the second catheter 130 and will flow into the inferior vena cava in its normal direction. Blood flow through the brain and the entire upper body will therefore be switched.

Figure 9A:
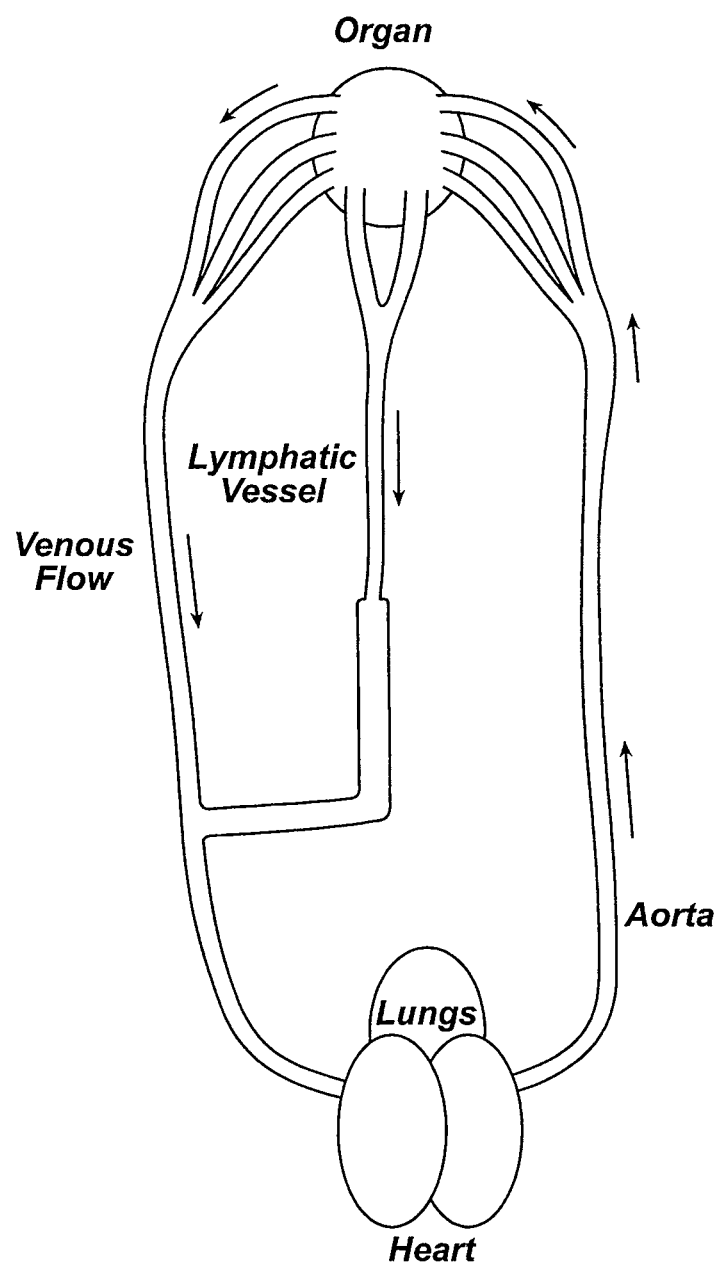
FIG. 9A is a diagram illustrating normal blood flow through the lymphatic vessels.
Figure 9B:
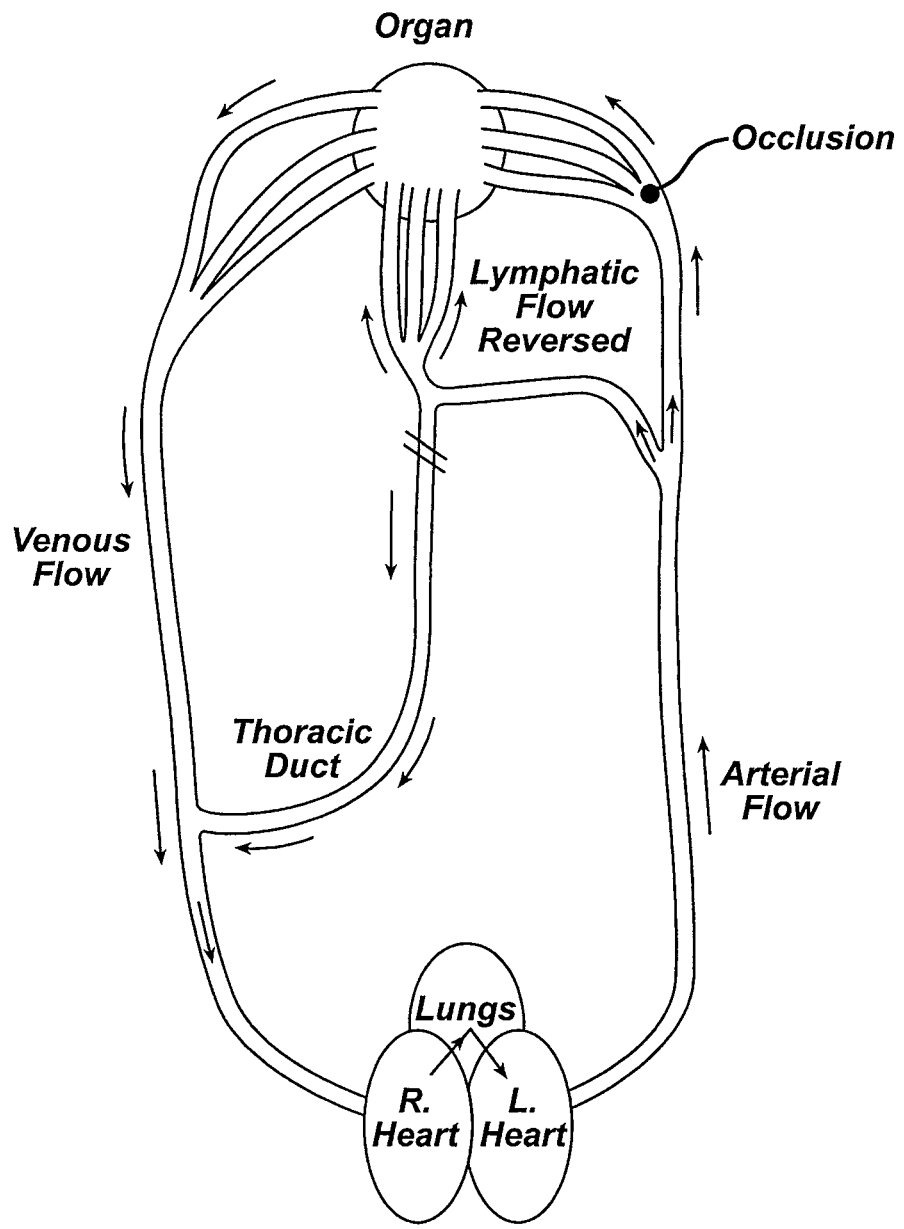
FIG. 9B is a diagram illustrating blood flow switched through a portion of the lymphatic vessels.
Figure 9C:
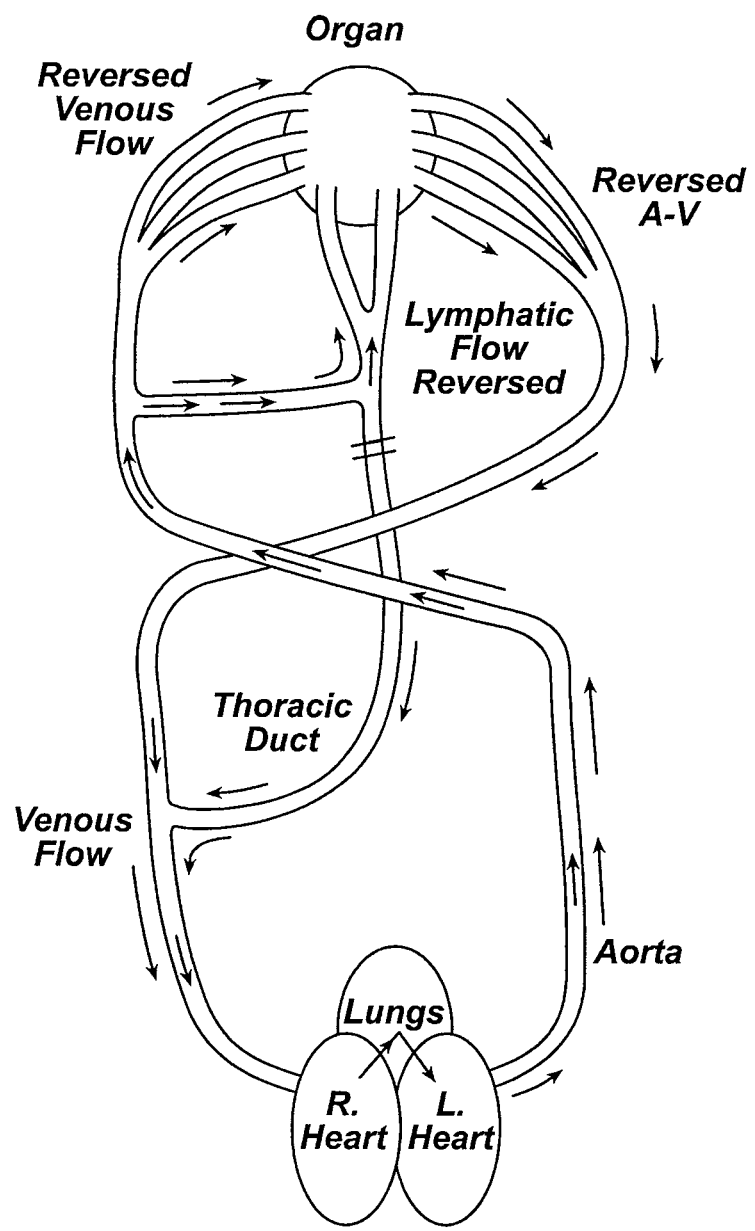
FIG. 9C is a diagram illustrating blood flow switched through the lymphatic vessels and through arterial and venous vessels coupled to an organ.

FIGS. 9A-9C illustrate additional embodiments for switching fluid flow in a body part. In these embodiments, the body part is the lymphatic system. FIG. 9A illustrates normal blood flow from the lungs and heart, through the aorta, to an organ, and exiting the organ through a venous vessel, which delivers the blood back to the heart. The blood also exits the organ through a lymphatic vessel, which eventually delivers the blood to the heart as well. In one embodiment, shown in FIG. 9B, blood flow can be switched through a portion of the lymphatic vessel such that a portion of the lymphatic vessel delivers blood to, rather than receives blood from, the organ. While catheters are not shown, a person skilled in the art will appreciate that the aforementioned flow control system can be used to redirect fluid flow as shown in FIG. 9B. Such reversal is particularly useful where a naturally occurring blockage, e.g., a thrombus T, has developed in the arterial supply to the organ as shown. In another embodiment, shown in FIG. 9C, blood flow can be switched through the entire arterial and venous supplies, including the lymphatic supply. Again, while catheters are not shown, a person skilled in the art will appreciate that a flow control system can be used to redirect blood flow as shown in FIG. 9C.

Figure 10A:
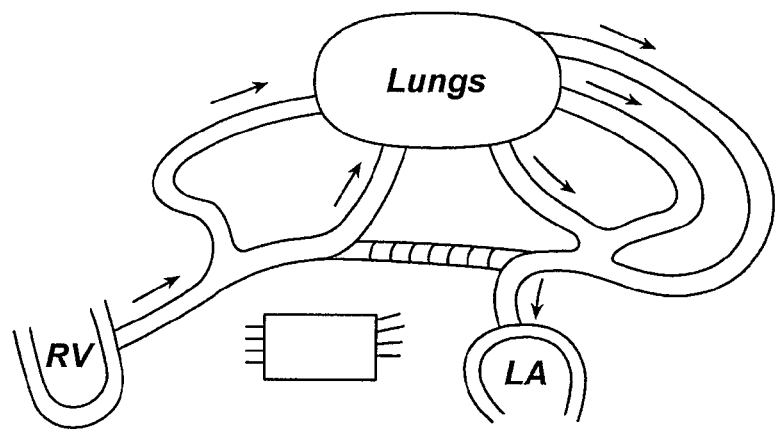
FIG. 10A is a diagram illustrating normal blood flow through the lungs.
Figure 10B:
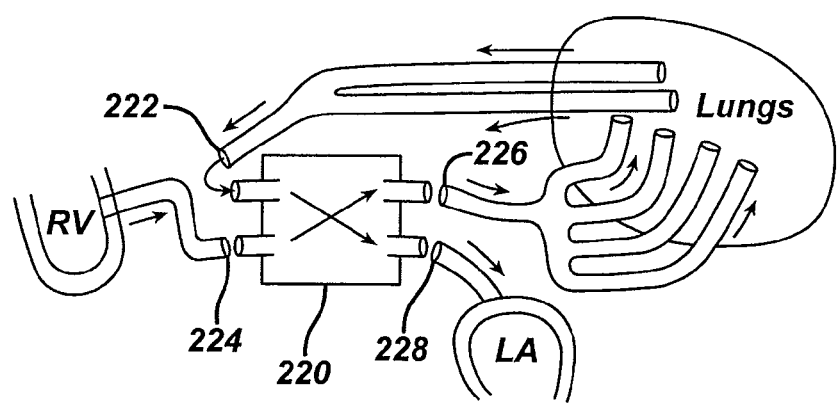
FIG. 10B is a diagram illustrating blood flow switched through the lungs.

FIGS. 10A-10B illustrate a method for switching blood flow through the lungs. During normal blood flow, as shown in FIG. 10A, blood flows into the lungs from the right ventricle RV through the pulmonary trunk and the pulmonary arteries and blood exits the lungs through the pulmonary veins and is delivered to the left atrium LA. Unlike with most organs, the arteries carry deoxygenated blood to the lungs and the veins receive oxygenated blood from the lungs. In order to switch blood flow through the lungs, as shown in FIG. 10B, a first catheter (not shown) can be implanted to form a first blockage in the venous supply such that a distal opening 222 is in fluid communication with the lungs and a proximal opening 224 is in fluid communication with the right ventricle RV. While only one distal opening 222 is shown, the catheter can optionally include branches with first and second openings to allow one opening to be positioned in the right pulmonary artery and the other opening to be positioned in the left pulmonary artery. A second catheter (not shown) can be implanted to form a second blockage in the arterial supply such that a distal opening 226 is in fluid communication with the lungs and a proximal opening 228 is in fluid communication with the left atrium LA. While only one distal opening 226 is shown, the catheter can optionally include multiple branches with first, second, third, and fourth openings to allow an opening to be positioned in each of the four pulmonary veins. Blood can thus flow from the right ventricle RV into the proximal opening 224 in the first catheter, where it is delivered to the flow control apparatus 220 which directs the blood to the second catheter, and in particular to the distal opening 226 in the second catheter. The blood flows out of the distal opening 226 in the second catheter and into the lungs in a direction opposite from normal. The blood will thus flow into the lungs through the pulmonary arteries in the switched direction and will flow out of the lungs into the pulmonary veins. The blood will be blocked from flowing to the right ventricle, and will thus enter the distal opening 222 in the first catheter and will flow through the hub and to the second catheter, where it will flow out of the proximal opening 228 in the second catheter to be delivered to the left atrium in its normal fluid flow direction.

Figure 11A:
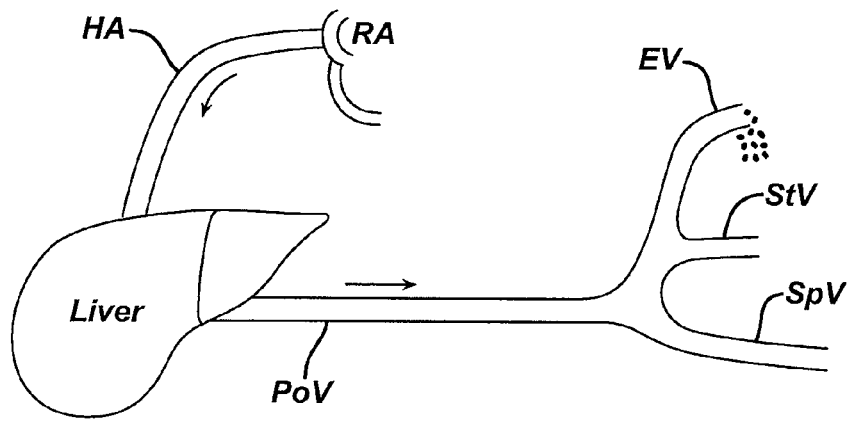
FIG. 11A is a diagram illustrating normal blood flow through the liver.

In another embodiment, the body part can be the liver. As shown in FIG. 11A, during normal blood flow, blood travels from gut area (esophagus, stomach and intestine) via the portal vein where it enters the liver. From the liver, blood travels via the hepatic veins into the right atrium. In cases of Portal Hypertension, the blood pressure inside the portal vein might be very high to cause bleeding in the esophagus or stomach (variceal bleeding) and might exceed the arterial blood pressure in some cases. In this case, reversal of flow will shift blood away from the portal circulation into the arterial systemic circulation. This might be a life saving treatment in acute cases. Also by having control over the pressure of blood inside the portal and hepatic side of the circulation, a regulated shunt to the systemic circulation can be controlled, for example using on and off shunting or grading of pressure/flow relation to maintain the highest filtration pressure possible while avoiding the risk of bleeding and minimizing the amount of blood mix between the portal and systemic circulations. The presence of portal blood inside the systemic circulation causes Hepatic Encephalopathy over time due to accumulation of toxins like Ammonia which escapes detoxification by the Liver.

Figure 11B:
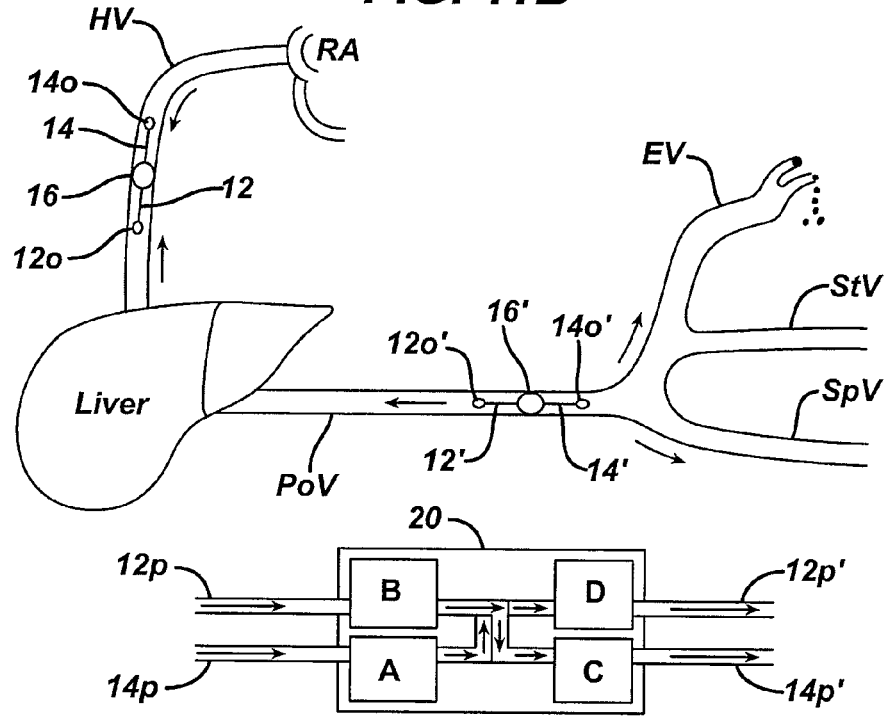
FIG. 11B is a diagram illustrating blood flow switched through the liver.

As shown in FIG. 11B, a first catheter (shown in part) is implanted in the hepatic vein HV and a balloon 16 is expanded to form a blockage such that a distal opening 120 in a first tubular member 12 is in fluid communication with the liver and a distal opening 140 in a second tubular member 14 is in fluid communication with the right atrium RA. A second catheter (shown in part) is implanted in the portal vein PoV and a balloon 16' is expanded to form a blockage such that a distal opening 120' in a first tubular member 12' is in fluid communication with the liver and a distal opening 140' in a second tubular member 14' is in fluid communication with the veins EV, StY, SpY. The first and second catheters can be coupled to a flow control apparatus 20, as previously explained, and the system can direct fluid flow to switch the normal flow through the liver. In particular, blood flowing toward the liver from the right atrium RA is blocked by the first balloon 16, and thus flows into the distal opening 140 in the first tubular member 14. The blood will flow through the first tubular member 14 in the catheter to the proximal end 14$p$ and into pump A. The flow control apparatus 20 will direct the blood from pump A to pump D, which is coupled to the proximal end 12$p'$ of the first tubular member 12 of the second catheter. The blood will flow through the first tubular member 12' and will exit the distal opening 120' to flow into the liver in a direction opposite from normal. The blood will thus flow through the liver in the switched direction and will enter the distal opening 120 in the first tubular member 12 of the first catheter, as it is blocked by balloon 16 from flowing into the right atrium. The blood will flow through the first tubular member 12 and will exit the proximal end 12$p$ and enter pump B. The flow control apparatus 20 directs blood from pump B to pump C, which is coupled to the proximal end 14$p'$ of the second tubular member 14 of the second catheter. The blood will flow through the second tubular member 14 and will exit the open distal end 140' to flow in its normal direction into the veins. While not shown, the flow control apparatus 20 can optionally include an accessory pump to perform detoxification of blood, removal of ammonia by ultra filtration, change in blood, physical, or chemical properties, administration of organ specific treatments, such as medications, depot form medications, genetic material, radioactive material, etc., or to harvest tissues or blood depending on the connections, etc. The flow control apparatus 20 can also be configured to control the blood pressure, increasing and decreasing the pressure between each pump to prevent continuous high pressure that causes bleeding, for example due a hemorrhage. Moreover, the apparatus 20 can maintain separation between the portal and system circulations to prevent hepatic encephalopathy.

A person skilled in the art will appreciate that flow switching can be performed to treat numerous conditions. For example, in other embodiments embolic ischemia secondary to occlusion of any limb arterial supply can be treated by arterial-venous switching to save the affected limb from gangrene. The treatment can also be used in cases of chronic vasculopathy secondary to diseases like diabetes, which mainly affects the arterial side and partially spares the venous side. Arterial-venous switching at the level of the femoral artery and the iliac artery, as previously discussed, can also be used to treat primary vascular diseases like Burger's disease. Such switching treatment might also provide effective in decreasing the reaction in small or medium sized vessels in the case of connection tissue diseases or vasculitidis that mainly affects the arterial side. Other applications include treatment of internal bleeding or uterine bleeding. In the case of severe acute bleeding that can be life threatening, an immediate arterial-venous switch of the main blood vessels supplying the specific anatomic location might be curative until permanent therapy is implemented. Sometimes the source of bleeding is either obscure or diffuse over a large raw area that can be difficult to control. In cases of uterine bleeding, sometimes hysterectomy is the only solution to prevent fatal bleeding. Arterial-venous switching in this case can be life saving while sparing the uterus until the wound is healed after a decrease of the blood pressure resulting from the switching. Arterial-venous switching may also provide new solutions to reperfusion of coronary vessels, by switching from atherosclerosis coronary arteries to partially spared coronary veins. Esophageal or stomach bleeding could also be treated by switching portal veins circulation partially to hepatic arterial circulation.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for switching blood flow in a body part, comprising:
   coupling a flow control system to the body part, the flow control system configured to provide a plurality of flow paths;
   delivering, with the flow control system configured to provide a first flow path, oxygenated blood flowing to a body part through a blood outflow vessel of the body part and providing oxygenated blood flowing out of the body part through a blood inflow vessel of the body part such that oxygenated blood enters the body part through the blood outflow vessel and oxygenated blood exits the body part through the blood inflow vessel; and
   delivering, with the flow control system configured to provide a second flow path, oxygenated blood flowing to a body part through a blood inflow vessel of the body part and providing oxygenated blood flowing out of the body part through a blood outflow vessel of the body part such that oxygenated blood enters the body part through the blood inflow vessel and oxygenated blood exits the body part through the blood outflow vessel.

2. The method of claim 1, wherein oxygenated blood is delivered using at least two catheters that are implanted to form blockages in the blood inflow and outflow vessels.

3. The method of claim 2, further comprising generating a negative pressure in at least one of the catheters to cause all oxygenated blood to enter the body part through the blood outflow vessel and all oxygenated blood to exit the body part through the blood inflow vessel.

4. The method of claim 2, wherein each blockage includes a distal side in fluid communication with the body part and a proximal side blocked from fluid communication with the body part, and further comprising redirecting with the at least two catheters fluid from the proximal side of the blood inflow vessel to the distal side of the blood outflow vessel and from the distal side of the blood inflow vessel to the proximal side of the blood outflow vessel.

5. The method of claim 2, wherein oxygenated blood is delivered using a pump mechanism.

6. The method of claim 1, wherein the body part comprises the brain and blood enters the brain through the jugular vein and blood exits the brain through the carotid artery.

7. The method of claim 1, wherein the body part comprises the heart and blood flows from the left side of the heart to the right side of the heart.

8. The method of claim 1, wherein the body part comprises the heart and blood enters the heart through the coronary sinus and blood exits the heart through the coronary artery.

9. The method of claim 1, wherein the blood inflow vessel comprises an arterial vessel and the blood outflow vessel comprises a lymphatic vessel, and wherein blood enters the body part through the lymphatic vessel and blood exits the body part through a venous vessel.

10. The method of claim 1, wherein the blood inflow vessel comprises an arterial vessel and blood outflow vessel comprises a lymphatic vessel, and wherein the blood enters the body part through the lymphatic vessel and a venous vessel and blood exits the body part through the arterial vessel.

11. The method of claim 1, wherein the body part comprises the liver and blood enters the liver through the hepatic veins and blood exits the liver through the hepatic artery and portal vein.

12. The method of claim 1, wherein the body part comprises the lungs and blood enters the lungs through the pulmonary veins and blood exits the lungs through the pulmonary arteries.

13. A method for switching blood flow in an arterial-venous system, comprising:
   forming a first blockage in a blood inflow vessel that delivers blood to a body part to prevent blood flow between a distal side of the first blockage in fluid communication with the body part and a proximal side of the first blockage blocked from communication with the body part;
   forming a second blockage in a blood outflow vessel that drains blood from the body part to prevent blood flow between a distal side of the second blockage in fluid communication with the body part and a proximal side of the second blockage blocked from communication with the body part; and
   redirecting blood from the proximal side of the first blockage to the distal side of the second blockage, and from the distal side of the first blockage into the proximal side of the second blockage such that oxygenated blood is provided to a body part through a blood outflow vessel of the body part and oxygenated blood flows out of the body part through a blood inflow vessel of the body part.

14. The method of claim 13, further comprising delivering oxygenated blood around the first blockage from the proximal side of the first blockage to the distal side of the first blockage to provide the oxygenated blood to the body part through the blood inflow vessel of the body part and providing oxygenated blood flowing out of the body part through a blood outflow vessel around the second blockage from the distal side of the second blockage to the proximal side of the second blockage such that oxygenated blood exits the body part through the blood outflow vessel.

15. The method of claim 13, wherein forming the first blockage comprises positioning a first catheter within the blood inflow vessel and inflating a balloon on the first catheter to form the first blockage, and wherein forming the second blockage comprises positioning a second catheter within the blood outflow vessel and inflating a balloon on the second catheter to form the second blockage, and wherein the first and second catheters each include at least one lumen formed therein that redirects blood.

16. The method of claim 15, wherein blood flows from the body part into a first lumen of the first catheter and out of a second lumen of the second catheter and into the blood outflow vessel, and from the blood inflow vessel into a second lumen of the first catheter and out of a first lumen of the second catheter and into the body part.

17. The method of claim 13, further comprising:
   forming a third blockage in a second blood inflow vessel that delivers blood to a body part to prevent blood flow between a distal side of the third blockage in fluid communication with the body part and a proximal side of the third blockage blocked from communication with the body part; and
   forming a fourth blockage in a second blood outflow vessel that drains blood from the body part to prevent blood flow between a distal side of the fourth blockage in fluid communication with the body part and a proximal side of the fourth blockage blocked from communication with the body part.

18. The method of claim 13, further comprising activating a pumping mechanism to redirect blood flow.

19. The method of claim 13, wherein the blood inflow and outflow vessels comprise arterial and venous vessels.

20. The method of claim 13, wherein the body part comprises the brain and the blood inflow vessel comprises the carotid artery and the blood outflow vessel comprises the jugular vein.

21. The method of claim 19, wherein the first blockage is formed by advancing a first catheter through the femoral artery to position a balloon on the first catheter within the carotid artery, and inflating the balloon to form the first blockage within the carotid artery, and the second blockage is formed by advancing a second catheter through the femoral vein to position a balloon on the second catheter within the jugular vein, and inflating the balloon to form the second blockage within the carotid artery.

22. The method of claim 21, wherein blood flowing from the heart and into the carotid artery on a proximal side of the first blockage flows through a first lumen in the first catheter and through a first lumen in the second catheter and is delivered to a distal side of the second blockage in the jugular vein such that the blood flows into the brain from the jugular vein, and wherein blood flowing from the brain and into the carotid artery on a distal side of the first blockage flows through a second lumen in the first catheter and through a second lumen in the second catheter and is delivered to a proximal side of the second blockage in the jugular vein such that the blood flows from the jugular vein toward the heart.

23. The method of claim 13, wherein the body part comprises the heart and the first and second blockages are formed such that blood flows from the left side of the heart to the right side of the heart.

24. The method of claim 13, wherein the body part comprises the heart and the first and second blockages are formed such that blood exits the heart through the coronary artery and enters the heart through the coronary sinus.

25. The method of claim 13, wherein the blood inflow vessel comprises an arterial vessel and the blood outflow vessel comprises a lymphatic vessel, and wherein the first and second blockages are formed such that blood enters the body part through the lymphatic vessel and blood exits the body part through a venous vessel.

26. The method of claim 13, wherein the blood inflow vessel comprises an arterial vessel and blood outflow vessel comprises a lymphatic vessel, and wherein the first and second blockages are formed such that blood enters the body part through the lymphatic vessel and a venous vessel and blood exits the body part through the arterial vessel.

27. The method of claim 13, wherein the body part comprises the liver and the first and second blockages are formed such that blood enters the liver through the hepatic veins and blood exits the liver through the hepatic artery and portal vein.

28. The method of claim 13, wherein the body part comprises the lungs and the first and second blockages are formed such that blood enters the lungs through the pulmonary veins and blood exits the lungs through the pulmonary arteries.

29. A method for switching blood flow, comprising:
forming a blockage in an artery, wherein blood normally flows toward the blockage on a first side of the blockage and blood normally flows away from the blockage on a second side of the blockage;
forming a blockage in a vein, wherein blood flows toward the blockage on a first side of the blockage and blood flows away from the blockage on a second side of the blockage;
delivering blood from the first side of the blockage in the artery to the first side of the blockage in the vein and delivering blood from the second side of the blockage in the artery to the second side of the blockage in the vein such that blood flow on the second side of the blockage in the artery and the first side of the blockage in the vein is switched to flow toward the blockage on the second side of the blockage in the artery and to flow away from the first side of the blockage in the vein.

30. The method of claim 29, further comprising delivering blood around the first blockage from the proximal side of the first blockage to the distal side of the first blockage to provide the oxygenated blood flowing away from the second side of the blockage in the artery and providing blood around the second blockage from the distal side of the second blockage to the proximal side of the second blockage such that oxygenated blood flows toward the first side of the blockage in the vein.

* * * * *